US008859223B1

(12) United States Patent
Franz et al.

(10) Patent No.: US 8,859,223 B1
(45) Date of Patent: Oct. 14, 2014

(54) COMPOSITIONS AND METHODS FOR IMAGING BETA-SECRETASE ACTIVITY IN LIVING CELLS AND ORGANISMS

(71) Applicant: Duke University, Durham, NC (US)

(72) Inventors: Katherine J. Franz, Durham, NC (US); Drew Folk, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/833,277

(22) Filed: Mar. 15, 2013

Related U.S. Application Data

(60) Provisional application No. 61/616,018, filed on Mar. 27, 2012.

(51) Int. Cl.
| | |
|---|---|
| *C12Q 1/37* | (2006.01) |
| *A61K 38/00* | (2006.01) |
| *G01N 33/573* | (2006.01) |
| *C07K 16/40* | (2006.01) |
| *G01N 21/64* | (2006.01) |

(52) U.S. Cl.
CPC .................................. *G01N 21/6486* (2013.01)
USPC ............................................. 435/23; 435/7.4

(58) Field of Classification Search
None
See application file for complete search history.

(56) References Cited

PUBLICATIONS

Mancini et al. "Beta-secretase as a target for Alzheimer's disease drug discovery: an overview of in vitro methods for characterization of inhibitors" Anal. Bioanal. Chem. (2011) 400: 1979-1996.*
Jinling Lu and Al. Visulization of b-secretase cleavage in living cells using a genetically encoded surface-dnisplayed FRET probe. Biochemical and Biophysical Research Communications 362 (2007) 25-30.
Shawn J. Stachel et al. Discovery of aminoheterocycles as a novel b-secretase inhibitor class: pH dependence on binding activity part 1. Bioorganic & Medicinal Chemistry Letters 19 (2009) 2977-2980.
Myungsok Oh et al. Cell-based assay for b-secretase activity. Analytical Biochemistry 323 (2003) 7-11.
Beth L. Pietrak et al. Biochemical and cell-based assays for characterization of BACE-1 inhibitors. Anal. Biochem. 342 (2005) 144-151.
Li-Na Hao et al. Antagonistic effects of ultra-low-molecular-weight heparin on Aβ25-35-induced apoptosis in cultured rat cortical neurons. Brain Research 1368 (2011) 1-10.
Yoshiari Shimmyo et al.. Flavonols and flavones as BACE-1 inhibitors: Structure—activity relationship in cell-free, cell-based and in silico studies reveal novel pharmacophore features. Biochimica et Biophysica Acta 1780 (2008) 819-825.
David R. Riddell et al. Compartmentalization of β-secretase (Asp2) into low-buoyant density, noncaveolar lipid rafts. Curr Biol. Aug. 21, 2001;11(16):1288-1293.

Peter J. Crouch et al. Mechanisms of A β mediated neurodegenerationin Alzheimer's disease. The International Journal of Biochemistry & Cell Biology 40 (2008) 181-198.
Maria L Bolognesi et al. Alzheimer's disease: new approaches to drug discovery. Curr Opin Chem Biol. Jun. 2009;13(3):303-308.
Francesca Mancini et al. Beta-secretase as a target for Alzheimer's disease drug discovery: an overview of in vitro methods for characterization of inhibitors. Anal Bioanal Chem (2011) 400:1979-1996.
Patrick C. May et al. Robust Central Reduction of Amyloid-β in Humans with an Orally Available, Non-Peptidic β -Secretase Inhibitor. The Journal of Neuroscience, Nov. 16, 2011 • 31(46):16507-16516.
Sang-Il Kim et al. Amyloid β Oligomerization Is Induced by Brain Lipid Rafts. Journal of Cellular Biochemistry 99:878-889 (2006).
Michael Hutton et al. Genetics of Alzheimer's disease. Essays Biochem. 1998;33:117-131.
Joanna M. Cordy et al. The involvement of lipid rafts in Alzheimer's disease (Review). Molecular Membrane Biology, Jan.-Feb. 2006; 23(1): 111-122.
Alex J. Laude and Ian A. Prior. Plasma membrane microdomains: organization, function and trafficking (Review). Molecular Membrane Biology, May-Jun. 2004, 21, 193-205.
Rolf Postina. A Closer Look at α-Secretase. Current Alzheimer Research, 2008, 5, 179-186.
Mikio Shoji et al. Production of the Alzheimer Amyloid βProtein by Normal Proteolytic Processing. Science, New Series, vol. 258, No. 5079, Genome Issue (Oct. 2, 1992), pp. 126-129.
Xiao-Ping Shi et al. Novel mutations introduced at the β-site of amyloid β protein precursor enhance the production of amyloid β peptide by BACE1 in vitro and in cells. Journal of Alzheimer's Disease 7 (2005) 139-148.
Cobos-Correa, A. et al. Membrane-bound FRET probe visualizes MMP12 activity in pulmonary inflammation. Nature Chemical Biology, vol. 5, No. 9, Sep. 2009, pp. 628-630.
V. Frisardi et al. Towards Disease-Modifying Treatment of Alzheimer's Disease: Drugs Targeting β -Amyloid. Current Alzheimer Research, 2010, 7, 40-55.
Saoussen Ben Halima and Lawrence Rajendran. Membrane Anchored and Lipid Raft Targeted β-Secretase Inhibitors for Alzheimer's Disease Therapy. Journal of Alzheimer's Disease 24 (2011) 143-152.
Fiona Gru Ninger-Leitch et al. Substrate and Inhibitor Profile of BACE (β-Secretase) and Comparison with Other Mammalian Aspartic Proteases. The Journal of Biological Chemistry vol. 277, No. 7, Issue of Feb. 15, pp. 4687-4693, 2002.

(Continued)

*Primary Examiner* — Suzanne M Noakes
*Assistant Examiner* — Gerard Lacourciere
(74) *Attorney, Agent, or Firm* — Nifong, Kiefer & Klinck, PLLC

(57) ABSTRACT

Molecular probes are provided for use in fluorescence microscopy procedures for monitoring beta-secretase enzyme (BACE) activity in living cells and organisms. The probes may be useful for monitoring Alzheimer's Disease-associated BACE in living cells. By fluorescing when hydrolyzed by BACE, the probes can allow for real-time spatial and temporal assessment of enzymatic activity without the need for mutated cell lines or antibodies. The molecular probes may also be used to screen libraries of potential BACE inhibitors or evaluate how external stimuli affect BACE activity.

22 Claims, 13 Drawing Sheets

(56) References Cited

PUBLICATIONS

Hidekuni Yamakawa et al. β-Secretase Inhibitor Potency Is Decreased by Aberrant β-Cleavage Location of the "Swedish Mutant" Amyloid Precursor Protein. The Journal of Biological Chemistry vol. 285, No. 3, pp. 1634-1642, Jan. 15, 2010.

David W. Klaver et al. Glycosaminoglycan-induced activation of the β-secretease (BACE1) of Alzheimer's disease. Journal of neurochemistry(2010) 112, 1552-1561.

Kristina Endres and Falk Fahrenholz. Upregulation of the α-secretase ADAM10—risk or reason for hope? FEBS Journal 277 (2010) 1585-1596.

Drew S. Folk and Katherine J. Franz. A Prochelator Activated by β-Secretase Inhibits Aβ Aggregation and Suppresses Copper-Induced Reactive Oxygen Species Formation. J. Am. Chem. Soc. 2010, 132, 4994-4995.

Danzhi Huang et al. In Silico Discovery of β-Secretase Inhibitors. J. Am. Chem. Soc. 2006, 128, 5436-5443.

Shawn J. Stachel et al. Structure-Based Design of Potent and Selective Cell-Permeable Inhibitors of Human β-Secretase (BACE-1). J. Med. Chem. 2004, 47, 6447-6450.

Miles Congreve et al. Application of Fragment Screening by X-ray Crystallography to the Discovery of Aminopyridines as Inhibitors of β-Secretase. J. Med. Chem. 2007, 50, 1124-1132.

James A. Lenhart et al. "Clicked" Bivalent Ligands Containing Curcumin and Cholesterol As Multifunctional Aβ Oligomerization Inhibitors: Design, Synthesis, and Biological Characterization. J. Med. Chem. 2010, 53, 6198-6209.

Yuan Cheng et al. From Fragment Screening to In Vivo Efficacy: Optimization of a Series of 2-Aminoquinolines as Potent Inhibitors of Beta-Site Amyloid Precursor Protein Cleaving Enzyme 1 (BACE1). J. Med. Chem. 2011, 54, 5836-5857.

Wenjin Yang et al. Aminoethylenes: A Tetrahedral Intermediate Isostere Yielding Potent Inhibitors of the Aspartyl Protease BACE-1. Journal of Medicinal Chemistry, 2006, vol. 49, No. 3.

Michael S. Malamas et al. Aminoimidazoles as Potent and Selective Human β-Secretase (BACE1) Inhibitors. J. Med. Chem. 2009, 52, 6314-6323.

Matthew L. Hemming et al. Identification of β-Secretase (BACE1) Substrates Using Quantitative Proteomics. PLoS One. Dec. 29, 2009;4(12):e8477.

Hao Cui et al. Effects of Heparin and Enoxaparin on APP Processing and Aβ Production in Primary Cortical Neurons from Tg2576 Mice. PLoS One. 2011;6(7):e23007.

Taeko Kakizawa et al. Evaluation of superior BACE1 cleavage sequences containing unnatural amino acids. Bioorganic & Medicinal Chemistry 19 (2011) 2785-2789.

John Hardy and Dennis J. Selkoe. The Amyloid Hypothesis of Alzheimer's Disease: Progress and Problems on the Road to Therapeutics. Science. Jul. 19, 2002;297(5580):353-356.

Lawrence Rajendran et al. Efficient Inhibition of the Alzheimer's Disease β-Secretase by Membrane Targeting. Science. Apr. 25, 2008;320(5875):520-523.

Rauk, Dalton Transactions, 2008, 10, 1273-1282.

Bertini, S. et al., Letters in Drug Design & Discovery, 2010, 7, 507-515.

* cited by examiner

SEQUENCE LISTING

```
<160> NUMBER OF SEQ ID NOS: 12

<210> SEQ ID NO 1
<211> LENGTH: 12
<212> TYPE: PRT
<213> ORGANISM: Artificial Sequence
<220> FEATURE:
<223> OTHER INFORMATION: synthentic peptide

<400> SEQUENCE: 1

Glu Val Asn Leu Asp Ala His Phe Trp Ala Asp Arg
1               5                   10

<210> SEQ ID NO 2
<211> LENGTH: 8
<212> TYPE: PRT
<213> ORGANISM: Artificial Sequence
<220> FEATURE:
<223> OTHER INFORMATION: synthetic peptide

<400> SEQUENCE: 2

Glu Val Asn Leu Asp Ala His Phe
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic peptide

<400> SEQUENCE: 3

Glu Val Asn Leu Asp Ala Glu Phe
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Glu Ile Asp Leu Met Val Leu Asp
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Glu Ile Asp Leu Ser Ser His Asp
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

Glu Val Asn Leu Ser Ser His Asp
1               5
```

```
<210> SEQ ID NO 7
<211> LENGTH: 8
<212> TYPE: PRT
<213> ORGANISM: Artificial Sequence
<220> FEATURE:
<223> OTHER INFORMATION: Synthetic peptide

<400> SEQUENCE: 7

Asp Glu Thr Leu Asp Ala His Phe
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide

<400> SEQUENCE: 8

Ala Pro Ser Leu Asp Ala His Phe
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide

<400> SEQUENCE: 9

Ala Ser Asn Leu Asp Ala His Phe
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X is the unnatural amino acid thienyl
<220> FEATURE:
<221> NAME/KEY: MISC_FEATURE
<222> LOCATION: (4)..(4)
<223> OTHER INFORMATION: X is the unnatural amino acid thienyl
<220> FEATURE:
<221> NAME/KEY: MISC_FEATURE
<222> LOCATION: (5)..(5)
<223> OTHER INFORMATION: X is the unnatural amino norvaline

<400> SEQUENCE: 10

Glu Ile Xaa Xaa Xaa Ala His Phe
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Glu Val Asn Phe Glu Val Glu Phe
1               5
```

```
<210> SEQ ID NO 12
<211> LENGTH: 4
<212> TYPE: PRT
<213> ORGANISM: Artificial Sequence
<220> FEATURE:
<223> OTHER INFORMATION: Synthetic peptide

<400> SEQUENCE: 12

Trp Ala Asp Arg
1
```

COMPOSITIONS AND METHODS FOR IMAGING BETA-SECRETASE ACTIVITY IN LIVING CELLS AND ORGANISMS

CROSS REFERENCE TO RELATED APPLICATIONS

This application claims priority to U.S. Provisional Patent Application No. 61/616,018, filed Mar. 27, 2012, the disclosure of which is incorporated herein by reference in its entirety.

STATEMENT OF GOVERNMENT SUPPORT

This invention was made with U.S. Government support under the National Institutes of Health grant no. 1RO1-GM084176-01. The U.S. Government has certain rights in the invention.

TECHNICAL FIELD

The present disclosure relates to a methods and compositions for imaging β-secretase (BACE) activity in living cells and organisms. Particularly, the present disclosure relates to BACE fluorescent molecular probes for imaging (BACE) activity in living cells and organisms.

BACKGROUND

The pathological hallmarks of Alzheimer's Disease (AD) are the insoluble neuritic plaques composed primarily of amyloid-beta (Aβ).[1] Aβ is a 37-43 amino acid peptide associated with a variety of neurotoxic events ranging from diminished integrity of the blood-brain barrier due to oxidized lipids of endothelial cell membranes, to accumulation of hyperphosphorylated tau leading to damaged synapses and neuronal cell death[2] Evidence of Aβ toxicity is widespread in the post-mortem AD brain and thus limiting its toxicity and preventing its accumulation have become popular goals of medicinal research.[3]

Production of Aβ results from sequential cleavage of a transmembrane protein called amyloid precursor protein (APP) by two proteases. β-secretase (BACE) is a membrane-associated aspartic protease that cleaves APP in the extracellular domain and creates the N-terminus of Aβ.[4] Subsequent cleavage by γ-secretase in the membrane domain creates the C-terminus and releases the toxic Aβ fragment.[5] While this process is normal for most cells[6] it is actually a minor APP processing pathway. The primary metabolic fate of APP is initial hydrolysis by α-secretase in the middle of the Aβ domain, thus precluding Aβ formation, followed by γ-secretase processing to release protein fragments from the membrane.[7] In contrast to Aβ however, the peptides resulting from α-secretase cleavage appear to have neuroprotective effects[8] Further implicating BACE as a facilitator of AD are observations that genetic mutations that either increase BACE cleavage or decrease α-secretase activity result in increased Aβ production and early-onset AD.[9] Conversely, experiments that inhibit BACE activity in mice by either gene knockdown, interfering RNA, or APP mutation, have proven to reduce amyloid plaque loads and restore cognitive abilities.[4] These results have led to an increased effort to design BACE inhibitors as therapeutic agents for AD.

Developing potent and specific BACE inhibitors has been challenging due to the broad substrate specificity and large active site of the enzyme.[10] A popular assay used to monitor inhibitor efficacy in vitro utilizes a FRET substrate that increases its fluorescence emission when hydrolyzed by BACE. Effective BACE inhibitors therefore suppress the fluorescence turn-on effect. This approach remains the standard in assaying in vitro BACE activity[11] and in fact, the reagents for this fluorescence assay are commonly sold together as kits by multiple chemical suppliers. Because this technique is amenable to high-throughput screening, it has been used extensively to identify BACE inhibitors.[12] Many of these seemingly promising inhibitors, however, are disappointingly inadequate at inhibiting BACE activity when assayed in cell models.

The failure in cellular activity of inhibitors is due in part to the cellular localization of active BACE enzyme. Even though BACE is expressed on the extracellular membrane of cells, it is inactive at pH 7.4 and thus does not cleave APP when exposed to the extracellular environment. BACE must be endocytosed to an early endosome where ATPase pumps protons into the endosomal lumen and lowers the pH to between 4-5 in order to gain activity.[13] Thus, inhibitors that do not specifically access these endosomal compartments are unable to inhibit BACE in cellular models. Add in challenges with bioavailability, metabolic clearance, and brain access, and it is clear why designing potent BACE inhibitors has been extremely difficult.[14]

Compounding design problems are the assays used to evaluate inhibitors in cells. The typical ELISA assays for determining cellular efficacy of these inhibitors are slow, expensive, and laborious. They often require genetic manipulations of the cell lines, several costly antibodies, and take multiple days.[15] An alternative FRET-based assay has been developed, but still requires genetic manipulation and cannot easily detect real-time fluorescence changes.[16]

Accordingly, there remains an unmet need for molecular probes to image real-time BACE activity in living cells and organisms that do not require the use of mutated cell lines or antibodies. The presently disclosed subject matter provides such BACE probes.

SUMMARY

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

One aspect of the present disclosure provides a molecular probe for beta-secretase (BACE), the probe comprising, consisting of, or consisting essentially of formula (I) A-B-C-D-E, wherein A is a fluorescent group, B is a BACE substrate module, C is a quenching group, D is at least one linker molecule, and E is a cell membrane anchor. In one embodiment, A and C comprise a Fluorescence Resonance Energy Transfer (FRET) pair. In one embodiment, A comprises a fluorophore 7-dimethylaminocoumarin-4-acetic acid (DMACA), B comprises a BACE substrate polypeptide set forth in SEQ ID NO: 1, C comprises a quenching group 4-(dimethylaminoazo)benzene-4-carboxylic acid (DABCYL), D comprises at least three PEG units, and E comprises a dihydrocholesterol moiety.

In one aspect, the present disclosure provides a method of using a probe of formula (I) for imaging beta-secretase activity in a live cell comprising, consisting of, or consisting essentially of: incubating the probe with the live cell; and exposing the cell to electromagnetic radiation such that a signal produced by the fluorescent group can be detected upon cleavage of the BACE substrate by the BACE activity in the cell. In one embodiment, the method further comprises adding a potential BACE inhibitor to the incubation of the probe with the live cell, wherein a decrease in the signal in the presence of the potential BACE inhibitor indicates inhibition of the BACE activity in the live cell by the potential inhibitor.

In one aspect, the present disclosure provides a method of using a probe for formula (I) for imaging beta-secretase activity in a living organism comprising, consisting of, or consisting essentially of: administering the probe to the organism; and exposing the orgamism to electromagnetic radiation such that a signal produced by the fluorescent group can be detected upon cleavage of the BACE substrate by the BACE activity in the organism. In one embodiment, the method further comprises administering a potential BACE inhibitor along with the administration of the probe to the living organism, wherein a decrease in the signal in the presence of the potential BACE inhibitor indicates inhibition of the BACE activity in the living organism by the potential inhibitor.

BRIEF DESCRIPTION OF THE DRAWINGS

The foregoing summary, as well as the following detailed description of various embodiments, is better understood when read in conjunction with the appended figures. For the purposes of illustration, there is shown in the Figures exemplary embodiments; however, the presently disclosed subject matter is not limited to the specific methods and exemplary embodiments disclosed.

Figure 1:
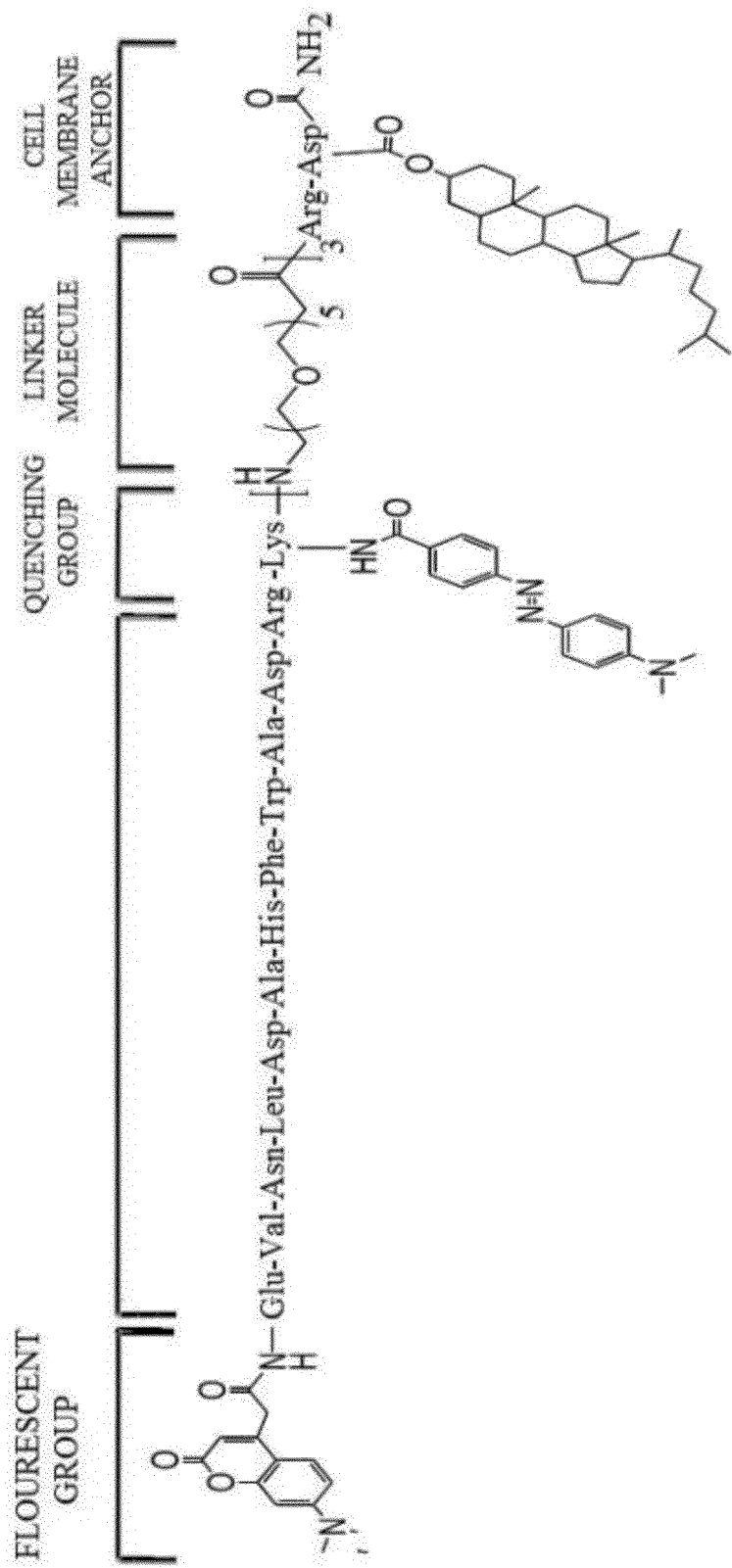
FIG. 1 is a schematic diagram of the structure of a BACE molecular probe (β-MAP) with key design features in accordance with one or more embodiments of the present disclosure.

DABCYL HPLC run on Eclipse XDB-C8 column with 0.1% formic acid H₂O: Acetonitrile gradient in accordance with one or more embodiments of the present disclosure. ESI-MS data show peaks that correspond to the +2H, +3H, and +4H ions of a parent compound with a mass of 2080.2. This agrees with the expected average mass of 2080.3 for this peptide. The expected average molecular weight was 2080.3 and the observed molecular mass (m) was 2080.2.

DETAILED DESCRIPTION

The presently disclosed subject matter now will be described more fully hereinafter with reference to the accompanying Figures, in which some, but not all embodiments of the presently disclosed subject matter are shown. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Unless otherwise defined, all technical terms used herein have the same meaning as commonly understood by one of ordinary skill in the art to which this disclosure belongs.

The term "polypeptide" is used in its broadest sense and for the purposes of the specification and claims includes, peptides, polypeptides, and proteins, as well as peptides, polypeptides, and proteins that contain one or more non-natural amino acids or any other chemical modification that allows the polypeptide to function as a β-secretase (BACE) substrate. In addition, for the purposes of the specification and claims, the term "polypeptide" is herein used interchangeably with the term "peptide".

The present disclosure relates to molecular probes for beta-secretase of the formula (I)

A-B-C-D-E, wherein A is a fluorescent group, B is a BACE substrate module, C is a quenching group, D is at least one linker molecule and E is a cell membrane anchor.

In their most basic form, the probes consist of five functional elements: (a) a fluorophore/fluorescent group; (b) a BACE substrate module; (c) a quenching group; (d) a linker moiety and (e) a cell membrane anchor.

The advantages of the BACE probes of the present disclosure include that the probes can be used to image BACE activity in living cells in real-time using fluorescence microscopy and the assay can be executed and processed in less than one day. Use of the BACE probes to image BACE activity in living cells does not require manipulation of the cell line or the use of antibodies. The probes can also be used for in vitro applications, eliminating the need for multiple chemical probes.

The present disclosure provides β-secretase (BACE) molecular probes. In one embodiment, BACE probes are provided that can be used to image BACE activity in living cells in real-time using fluorescence microscopy. In one embodiment, a non-toxic BACE probe, called β-MAP for β-secretase Membrane-Anchored Probe, is provided and illustrated in FIG. 1. The β-MAP probe is a fluorescence resonance energy transfer (FRET)-based probe. The β-MAP structure includes a fluorescent group 7-dimethylaminocoumarin-4-acetic acid, ("DMACA") attached at the N-terminus of the BACE peptide substrate module. The BACE peptide substrate is in this case the amino acid sequence EVNLDAH-FWADR (SEQ ID NO: 1). Appended to the peptide substrate at the C-terminus is a lysine residue with a quenching group (4-(dimethylaminoazo)benzene-4-carboxylic acid ("DABCYL") attached to the ε-amine side chain. A linker molecule (polyethylene glycol) provides a flexible spacer between the BACE substrate and a cell membrane anchor (dihydrocholesterol modified aspartic acid in this case).

In certain embodiments, groups A and C may be chosen by those skilled in the art dependent on the application for which the probe is intended. A and C may be independently of each other a spectroscopic probe such as a fluorophore, a quenching group or chromophore, a magnetic probe, a contrast reagent, a molecule which is one part of a specific binding pair which is capable of specifically binding to a partner, a molecule which is a substrate for an enzyme, a molecule covalently attached to a polymeric support, a dendrimer, a glass slide, a microtiter plate known to those proficient in the art, or a molecule possessing a combination of any of the properties listed above.

In certain embodiments, Groups A and C are spectroscopic probes. In certain embodiments, A is one member and C is the other member of two interacting spectroscopic probes NC, wherein energy can be transferred non-radiatively between the donor and acceptor (quenching group) through either dynamic or static quenching. Such said pair of label NC changes its spectroscopic properties upon reaction/cleavage through the corresponding beta-secretase. An example of such a pair of probes NC is a FRET (Fluorescence resonance energy transfer) pair, e.g. a fluorescent probe covalently labeled at one end (e.g. A) with a donor (reporter), and the another position (C) with an acceptor (quenching group), or vice versa.

In some embodiments, A is a donor (reporter) and C is an acceptor (quenching group), or A is a quenching group and C is a reporter. In using this probe, the reaction of the beta-secretase with the probe will lead to a change in fluorescence. The reporter-quenching group distance within the double labeled substrate is changed upon reaction with the BACE leading to a spatial separation of reporter and quenching group which causes the appearance of fluorescence or change of the emission wavelength. A broad selection of reporter groups may be used as label A or C, respectively, including e.g. near infra-red emitting fluorophores. The substrate containing reporter and quenching group remains dark until it reacts with the BACE, whereupon the reaction mixture is "lit up" switching on the fluorophore emission, since the reporter label and the quencher label are now spatially separated. Fluorescence quenching and energy transfer can be measured by the emission of only one of the two labels, the quenched or energy donor label. When energy transfer occurs and the energy accepting label is also fluorescent, the acceptor label fluorescence can also be measured. A donor label of these two interacting label can be chosen from chemoluminescent donor probes which eliminates the need of an excitation lamp and reduces acceptor background fluorescence. The mentioned particular method using such double-labelled substrates is useful to determine reaction kinetics based on fluorescence time measurements, and may be applied in vivo as well as in vitro.

Appropriate pairs of reporters and quenchers can be chosen by those skilled in the art. Typically reporter and quencher are fluorescent dyes with large spectral overlap as, for example, fluorescein as a reporter and rhodamine as a quencher. Other quenchers are gold clusters, and metal cryptates.

In some embodiments, the quenchers comprise "dark quenchers", i.e. dyes without native fluorescence having absorption spectra that overlap with the emission spectra of common reporter dyes leading to maximal FRET quenching. Furthermore pairs of dyes can be chosen such that their absorption bands overlap in order to promote a resonance dipole-dipole interaction mechanism within a ground state complex (static quenching).

In one embodiment, A and C comprise a FRET pair. In some embodiments, A is a fluorophore selected from the group consisting of DMACA, Alexa 350, dimethylaminocoumarin, 5/6-carboxyfluorescein, Alexa 488, ATTO 488, DY-505, 5/6-carboxyfluorescein, Alexa 488, Alexa 532, Alexa 546, Alexa 555, ATTO 488, ATTO 532, tetramethylrhodamine, Cy 3, DY-505, DY-547, Alexa 635, Alexa 647, ATTO 600, ATTO 655, DY-632, Cy 5, DY-647 or Cy 5.5. In certain embodiments, A comprises DMACA.

In other embodiments, C comprises a quencher selected from DABSYL, BHQ 1, QSY 35, BHQ 2, QSY 9, ATTO 540Q, BHQ 3, ATTO 612Q and QSY 21. In certain embodiments, C comprises DABCYL.

In one embodiment of the BACE probe, B comprises a BACE substrate polypeptide that is cleaved by the BACE enzyme. Preferably, BACE has a high degree of specificity for the BACE substrate polypeptide. The polypeptide substrates can be any one of the polypeptides set forth in SEQ ID NO's: 1-6 and 10-11, the amino acid sequences of which are shown in Table I below. The polypeptide substrates can also be polypeptides that are conservatively substituted variants of SEQ ID NO's: 1-6 and 10-11. In one embodiment, the polypeptide can be the polypeptide set forth in SEQ ID NO: 1.

TABLE I

BACE substrate polypeptides

| Amino acid Sequence | SEQ ID NO |
| --- | --- |
| EVNL-DAHFWADR | 1 |
| EVNL-DAHF | 2 |
| EVNL-DAEF | 3 |
| EIDL-MVLD | 4 |
| EIDL-SSHD | 5 |
| EVNL-SSHD | 6 |
| DETL-DAHF | 7 |
| APSL-DAHF | 8 |
| ASNL-DAHF | 8 |
| EI(Thi)(Thi)-(Nva)AHF | 10 |
| EVNF-EVEF | 11 |

Amino acid single letter abbreviations are listed with a (-) representing the BACE cleavage site. (Thi) represents the unnatural amino acid thienyl and (Nva) represents the unnatural amino acid norvaline.

In one embodiment, the polypeptide substrates can be any one of the polypeptides set forth in SEQ ID NO's: 2-6 and 10-11 further including 4 additional amino acids at the polypeptide C-terminus. In one example, the 4 additional amino acids can be WADR (SEQ ID NO: 12). In another example, the 4 additional amino acids can be any amino acid. In another example, 1 of the 4 additional amino acids can be a tryptophan and the remaining 3 amino acids can be any amino acid. In another example, the first of the 4 additional amino acids can be a tryptophan and the remaining 3 amino acids can be any amino acid. The tryptophan residue can be included to facilitate concentration determination by taking advantage of the absorptivity of tryptophan's indole side chain. In another example, the first of the 4 additional amino acids can be a tryptophan and the last of the remaining 3 amino acids can be an arginine or a lysine. In another example, the last of the 4 additional amino acids can be an arginine or a lysine and the first 3 amino acids can be any amino acid. The arginine and lysine residues have side chains that are positively charged at neutral pH, which can aid solubility of the BACE probe in aqueous solution. Inclusion of the WADR (SEQ ID NO: 12) at the polypeptide C terminus may also prevent the bulky quenching group (DABCYL, in the case of β-MAP) from interfering in BACE hydrolysis.

Group D is a linker group and is used to provide the correct spacing and orientation for the FRET peptide hydrolyzed by the beta-secretase in the cells. As used herein, the term "linker" refers to any constituent that links stabilizing moieties. Typically the linker does not interfere with the reaction of a selected enzyme target nor with the detection of Groups A and/or C, but may provide additional benefits, such as increased solubility, correct orientation and the like. In some embodiments, the linker may be constructed such as to be cleaved at some point in time. The linker group is chosen in the context of the envisioned application, i.e., in context of an activity based imaging probe for a specific purpose. Suitable linking groups include, but are not limited to, $C_6$-$C_{30}$ alkyl groups, $C_6$-$C_{30}$ substituted alkyl groups, polyols, polyethers (e.g., polyethyleneglycol [PEG]), polyamines, polyamino acids, polysaccharides and combinations thereof. In certain embodiments, the linker comprises PEG.

The number of linking units is also important in ensuring the proper function of the probe. An incorrect number of linking molecules can prevent the FRET peptide (Group A) from being oriented such that it can be hydrolyzed by beta-secretase in the cell. In preferred embodiments, the linking molecules force the FRET peptides to be oriented from the C-terminus to the N-terminus as it extends from the cell membrane. Hence, in certain embodiments the linker group comprises at least one linking group, more preferably at least three linking groups.

Group E comprises a cell membrane anchor moiety. Group E can comprise a cholesterol moiety or a dihydrocholesterol moiety. The dihydrocholesterol moiety can be an aspartate modified dihydrocholesterol moiety. The cholesterol or the dihydrocholesterol moiety can be attached to the linker molecule through a residue having a positive charge. The residue having the positive charge can comprise arginine. The residue having the positive charge aids solubility and may prevent the probe from becoming buried in the cell membrane past the cholesterol.

In one embodiment of the BACE probe of formula (I), A comprises DMACA, B comprises a BACE substrate polypeptide set forth in SEQ ID NO: 1, C comprises DABCYL, D comprises at least three PEG units, and E comprises a dihydrocholesterol moiety.

The probes described herein may be used in a variety of in vitro and in vivo assays to monitor, image, and assess beta-secretase activity.

In one aspect, the present disclosure provides a method of using a probe of formula (I) for imaging beta-secretase activity in a live cell comprising, consisting of, or consisting essentially of: incubating the probe with the live cell; and exposing the cell to electromagnetic radiation such that a signal produced by the fluorescent group can be detected upon cleavage of the BACE substrate by the BACE activity in the cell. The method can further include creating an image from the detected signal. The method can further include adding a potential BACE inhibitor to the incubation of the probe with the live cell, wherein a decrease in the signal in the presence of the potential BACE inhibitor indicates inhibition of the BACE activity in the live cell by the potential inhibitor. In this manner, the activity of potential BACE inhibitors can be assessed inside the living cell. This allows for determination of whether or not the potential inhibitor will actually function as an inhibitor in vivo, for example, by being able to access the correct location inside the cell.

In yet another aspect, the present disclosure provides a method of using a probe for formula (I) for imaging beta-secretase activity in a living organism comprising, consisting of, or consisting essentially of: administering the probe to the living organism; and exposing the organism to electromagnetic radiation such that a signal produced by the fluorescent group can be detected upon cleavage of the BACE substrate by the BACE activity in the organism. The method can further include creating an image from the detected signal. The method can further include administering a potential BACE inhibitor along with the administration of the probe to the living organism, wherein a decrease in the signal in the presence of the potential BACE inhibitor indicates inhibition of the BACE activity in the living organism by the potential inhibitor. In this manner, the activity of potential BACE inhibitors can be assessed in living organisms. This allows for determination of whether or not the potential inhibitor will actually function as an inhibitor in vivo, for example, by being able to access the correct location inside the cell.

EXAMPLES

The following Examples have been included to provide guidance to one of ordinary skill in the art by way of illustration and not by way of limitation for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Structure of BACE Molecular Probe

One structure of a beta-secretase (BACE) molecular probe (β-MAP) is illustrated in FIG. 1. This BACE molecular probe contains multiple important design features. For example, a fluorescent group (7-dimethylaminocoumarin-4-acetic acid, "DMACA") is attached at the N-terminus of the BACE peptide substrate module. The BACE peptide substrate is in this case the amino acid sequence EVNLDAHFWADR (SEQ ID NO: 1). Appended to the peptide substrate at the C-terminus is a lysine residue with a quenching group (4-(dimethylaminoazo)benzene-4-carboxylic acid, "DABCYL") attached to the ε-amine side chain. A linker molecule (polyethylene glycol) provides a flexible spacer between the BACE substrate and a cell membrane anchor (dihydrocholesterol modified aspartic acid in this case).

BACE Substrate:

The BACE substrate shown in FIG. 1 for BACE molecular probe β-MAP consists of the sequence EVNLDAHFWADR (SEQ ID NO: 1). The first eight amino acids of this sequence are responsible for BACE enzyme recognition and are similar to residues 668-675 of the so-called Swedish mutant APP. In the peptide sequence of the β-MAP molecular probe, histidine has been substituted for glutamic acid at position 7 relative to the APP mutant (the sequence of this mutation is shown in SEQ ID NO: 2 in Table I below). The Swedish mutant APP demonstrates a 60-fold increase in Kcat/KM as compared to wild type BACE. In addition, people with the Swedish mutation are more likely to develop early onset Alzheiemer's Disease, likely as a result of increased BACE activity. For these reasons, peptide sequences having certain of the APP mutations were chosen for inclusion among the BACE polypeptide substrates for use in the BACE molecular probes of the present disclosure.

In the amino acid sequence of the BACE substrate module shown in FIG. 1, the BACE enzyme cleavage site is between the leucine and aspartic acid at positions 4 and 5, respectively. The remaining last 4 amino acid residues were incorporated into the substrate as a tryptophan-containing tag to facilitate concentration determination by taking advantage of the absorptivity of tryptophan's indole side chain (5625 $M^{-1}$ $cm^{-1}$ λmax=280 nm). Thus, the tryptophan tag of the BACE substrate is not required for recognition of the substrate by the BACE enzyme. The tryptophan does not significantly interfere with enzyme recognition or proteolysis, likely because it can be positioned outside the active site as was observed in the crystal structure of BACE complexed with a peptide inhibitior. The tag also contains a C-terminal arginine (R) residue, which has a guanidinium side chain that is positively charged at neutral pH and aids solubility in aqueous solution. The tag may also prevent the bulky quenching group (DABCYL, in the case of (3-MAP) from interfering in BACE hydrolysis.

In order to evaluate a range of peptide amino acid sequences as BACE substrates for the probes, the peptides shown below in Table II were incubated with BACE enzyme under conditions suitable for enzyme activity and the percent cleavage after 10 hr was determined by LC-MS. The data are shown below in Table II. Thus, in addition to SEQ ID NO: 1 present in β-MAP, the peptide sequences corresponding to SEQ ID NO's: 2-6 and 10-11 can also be useful as BACE substrates in the BACE probes of the present disclosure. For example, the specific BACE substrate sequence can be chosen based on the level of cleavage desired for a particular use for which the probe will be utilized. In can be envisioned that a higher or a lower amount of BACE probe cleavage could be desirable based on the different uses of the BACE probes.

TABLE II

Evaluation of peptides as BACE substrates

| Peptide Sequence | SEQ ID NO | Percent Cleavage after 10 hr Incubation with BACE |
|---|---|---|
| EVNL-DAHF | 2 | 50% |
| EVNL-DAEF | 3 | 50% |
| EIDL-MVLD | 4 | 20% |
| EIDL-SSHD | 5 | 5% |
| EVNL-SSHD | 6 | 3.5% |
| DETL-DAHF | 7 | 1% |
| APSL-DAHF | 8 | 0.5% |
| ASNL-DAHF | 8 | Not Detected |
| EI(Thi)(Thi)-(Nva)AHF | 10 | 25% |
| EVNF-EVEF | 11 | 85% |

Amino acid single letter abbreviations are listed with a (-) representing the BACE cleavage site. (Thi) represents the unnatural amino acid thienyl and (Nva) represents the unnatural amino acid norvaline.

Thus, for the polypeptide substrate in the BACE substrate module of the BACE probes of the present disclosure, the polypeptides can be any one of SEQ ID NO's: 1-6 and 10-11. In addition, the BACE substrate polypeptides, SEQ ID NO's: 2-6 and 10-11, can have an additional 4 amino acids at the C-terminus. In one example, the 4 additional amino acids can be WADR (SEQ ID NO: 12). In another example, the 4 additional amino acids can be any amino acid. In another example, 1 of the 4 additional amino acids can be a tryptophan and the remaining 3 amino acids can be any amino acid. In another example, the first of the 4 additional amino acids can be a tryptophan and the remaining 3 amino acids can be any amino acid. In another example, the first of the 4 additional amino acids can be a tryptophan and the last of the remaining 3 amino acids can be an arginine or a lysine. In another example, the last of the 4 additional amino acids can be an arginine or a lysine and the first 3 amino acids can be any amino acid.

FRET Pair.

Figure 2:
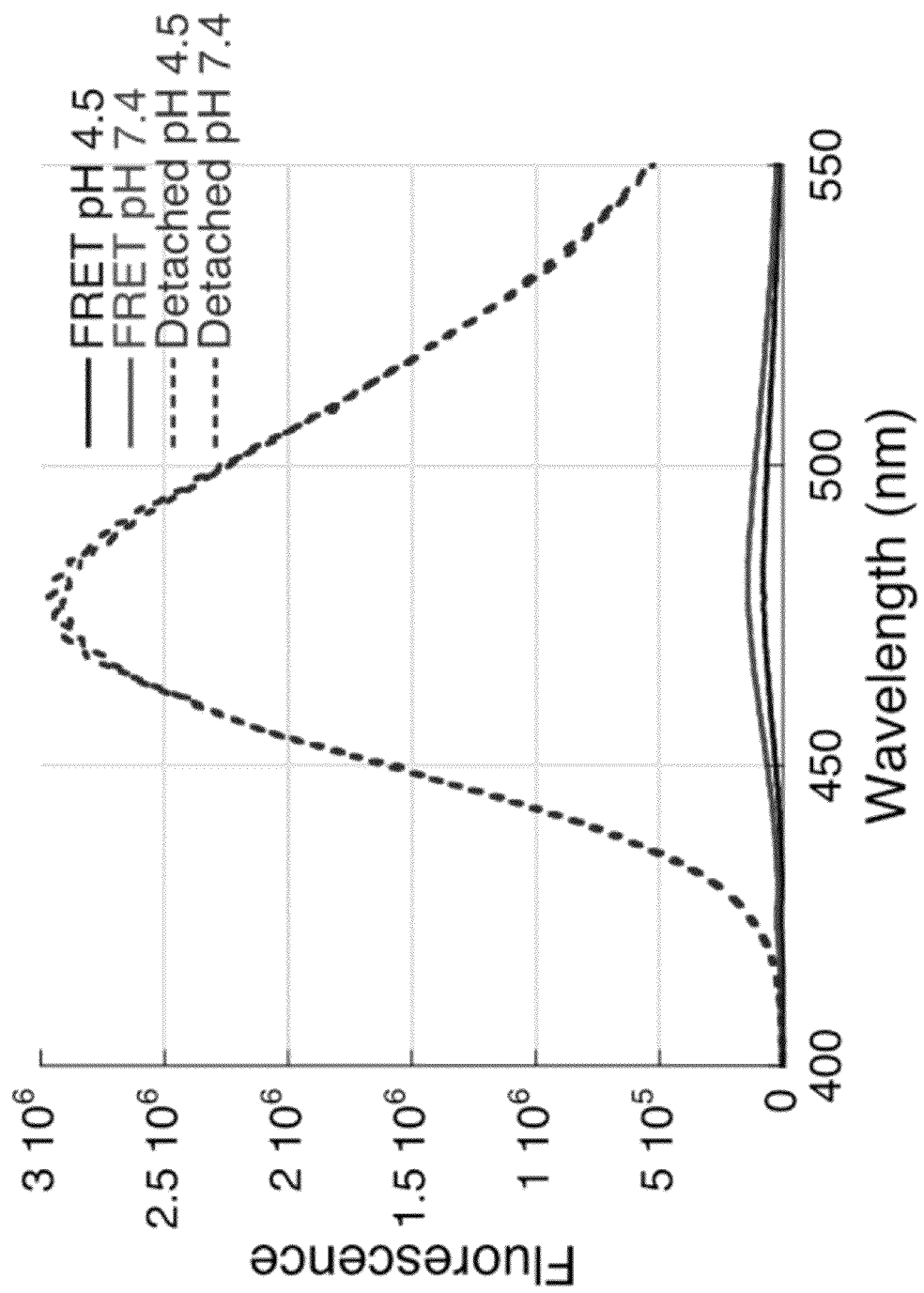
FIG. 2 is a graph showing the fluorescence properties of a DMACA-DABCYL FRET pair in accordance with one or more embodiments of the present disclosure. Solutions containing equimolar mixtures of 5 μM DMACA and DABCYL at either pH4.5 or pH 7.4 (dashed lines) show a robust emission spectra. The significantly diminished emission spectra of the DMACA-DABCYL FRET pair when the pair is attached to either end of the polypeptide SEQ ID NO: 1 (5 μM, solid lines) shows that DABCYL efficiently quenches DMACA at both pH's when included in a structure as a BACE probe.

While a range of FRET pairs may be useful in the BACE probes of the present disclosure, the DMACA-DABCYL FRET pair was chosen for further studies based in part on the DMACA excitation (370 nm) and emission (480 nm) properties being highly compatible with live cell fluorescence microscopy. The DMACA-DABCYL FRET pair was characterized as follows. First, 2 mM stock solutions of DMACA and Fmoc-Lys(DABCYL)-OH were prepared by dissolving the lyophilized powder in DMSO. Stocks were diluted to 5 µM in 3 mL of either 0.1M Sodium Acetate Buffer pH4.5 or 20 mM HEPES buffer (no salt) pH7.4 (0.25% DMSO). Solutions were transferred to a 1 cm fluorescence cuvette and the fluorescence spectrum recorded with 370 nm excitation. The fluorescence of DMACA was similar at both pH's (see FIG. 2). To evaluate the ability of DABCYL to efficiently quench DMACA fluorescence, the pair was conjugated to either end of the SEQ ID NO: 1 peptide to yield the peptide sequence DMACA-EVNLDAHFWADR-K(DABCYL) (SEQ ID NO: 1-FRET). The lyophilized peptide was dissolved in DMSO and further diluted in each buffer to yield a final concentration of 5 µM. In FIG. 2, solutions containing equimolar mixtures of 5 µM DMACA and DABCYL in either 0.1M NaOAc buffer pH4.5 or 20 mM HEPES buffer pH7.4 (dashed lines) show robust emission. The significantly diminished emission spectra of the SEQ ID NO: 1-FRET peptide (5 µM, solid lines) shows that DABCYL efficiently quenches DMACA at both pH's when the pair is attached to either end of the SEQ ID NO: 1 peptide. $\lambda_{ex}$=370 nm. This property is useful as the probe can operate in the acidic environment of an endosome as well as in the neutral extracellular media.

The DABCYL quenching group has a broad absorbance band between 420-520 nm and does not fluoresce making it an effective 'dark quencher' for the DABCYL group. The DABCYL quenching group was attached to the substrate through the ε-amine group of a lysine attached to the C-terminus of the BACE probe substrate. In addition to the desirable excitation and emission properties, the DABCYL-DABCYL FRET pair concurrently accomplished the second goal of the probe design, which was to avoid steric interference with BACE hydrolysis. A rhodamine-fluorescein pair was initially employed due to its visible excitation/emission wavelengths, but this substrate was unable to be efficiently cleaved by BACE in the system studied (data not shown).

Linker Molecule:

A linker molecule was chosen for the ε-MAP molecular probe for the following reasons. Three successive polyethylene glycol (PEG) units were determined to provide the correct spacing and orientation for the FRET peptide to be hydrolyzed by BACE in cells. Attachment of the PEG groups adjacent to the DABCYL forces the FRET peptide to be oriented from the C-terminus to the N-terminus as it extends from the cell membrane analogous to APP. Experiments with a cholesterol-anchored peptide BACE inhibitor have demonstrated that attachment of the PEG-anchor group to the N-terminus effectively reverses the chain direction and prevents BACE recognition.[17] The length of the PEG chain was also carefully chosen. APP contains 28 residues between the BACE cleavage site and the cell membrane.[5] The PEG linker molecule chosen provides for the equivalent of 29 residues between the membrane anchor and the hydrolysis site. Recent reports have suggested that the length of the linker is not strictly important, but that too short a linker could alter specificity or prevent hydrolysis,[13a] PEG also helps the solubility of the probe in aqueous solutions and is metabolically stable.

Cell Membrane Anchor.

The cell membrane anchor was chosen for the following reasons. The cell membrane anchor shown in FIG. 1 is composed of a dihydrocholesterol moiety attached to the linker molecule through use of an arginine aspartic acid dipeptide. The dihydrocholesterol moiety is an aspartate-modified dihydrocholesterol moiety and the arginine was included to add an additional positive charge to the BACE probe. The positive charge aids solubility and also ensures the probe does not get buried in the membrane past the cholesterol. The dihydrocholesterol moiety on the C-terminus provides a targeting vector to not only attach the probe to cell membranes, but more specifically to lipid raft compartments. Lipid rafts are microdomains within the cell membrane that contain high amounts of saturated phospholipids and cholesterol and are distinct from the largely unsaturated phospholipids of the surrounding bilayer.[19] Raft domains are a site of Aβ production and oligomerization[20] and significant amounts of BACE have been shown to localize in lipid rafts.[21]

The dihydrocholesterol moiety was shown to localize a probe to lipid rafts of the cell membrane using a probe designed such that the BACE polypeptide substrate SEQ ID NO: 1 would not be cleaved by the BACE enzyme in a cellular setting because the substrate sequence would be ill-positioned within the membrane. The probe was designed with a fluorescein group at the N-terminus and a dihydrocholesterol cell anchoring group at the C-terminus to enable visualization of the cellular localization of the probe. Specifically, the probe used in this experiment contained a fluorescein conjugated to the N-terminus of the SEQ ID NO: 1 peptide and the cholesterol-modified aspartic acid tethered directly to the C-terminus without the PEG linker (see FIG. 3). This construction prevents BACE from hydrolyzing SEQ ID NO: 1 peptide and releasing the chromophore.

The localization experiment was performed as follows. HeLa cells were plated on a 35 mm dish with 1.5 coverglass (MATTEK CORP.) in 2 mL complete growth medium and allowed to grow to about 50% confluence. On the day of the experiment, growth media was removed and cells were washed 1× with PBS. Next, 2 µM of the probe was dissolved in OptiMEM (0.1% DMSO) and incubated on the cells for 3 hrs at 37° C. and 5% $CO_2$. After incubation, media was removed and cells were washed 1× with PBS. Lipid rafts were labeled according to manufacturer's instructions (INVITROGEN). Briefly, cholera toxin subunit B (CT-B) conjugated to ALEXAFLUOR 594 was dissolved in PBS and diluted in chilled complete growth media. This solution was added to the cells and incubated at 4° C. for 10 min. After incubation, cells were washed 2× with PBS. Anti-cholera toxin subunit B rabbit serum was added to chilled complete growth media and incubated with cells for an additional 15 min at 4° C. Cells were again washed 2× with PBS and 2 mL OptiMEM was added for microscopy. Fluorescence microscopy was performed on a LEICA SP5 confocal microscope. Fluorescein labeled substrate was visualized using an Argon 488 nm laser for excitation and green emission filter while Lipid Rafts were visualized with HeNe 594 nm laser with red emission filter. No signal was observed when the excitation wavelengths were switched indicating there was no bleed-through between the red and green channels.

Figure 3:
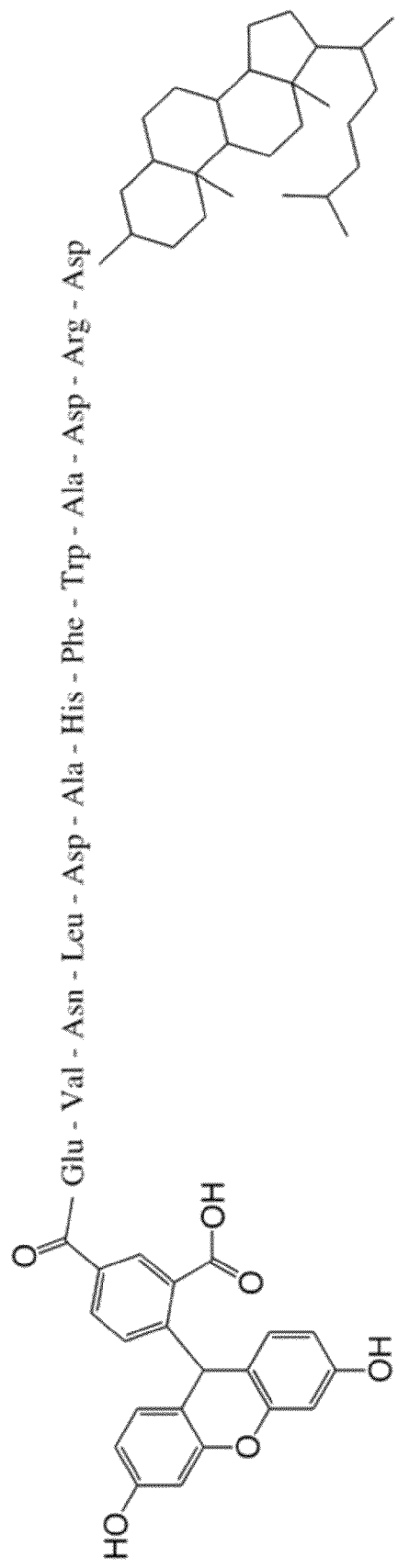
FIG. 3 is a schematic diagram of a structure of a BACE probe designed such that the BACE polypeptide substrate would not be cleaved by the BACE enzyme in accordance with one or more embodiments of the present disclosure. The probe was designed with a fluorescein group at the N-terminus and a dihydrocholesterol cell anchoring group at the C-terminus to enable visualization of the cellular localization of the probe.
Figure 4:
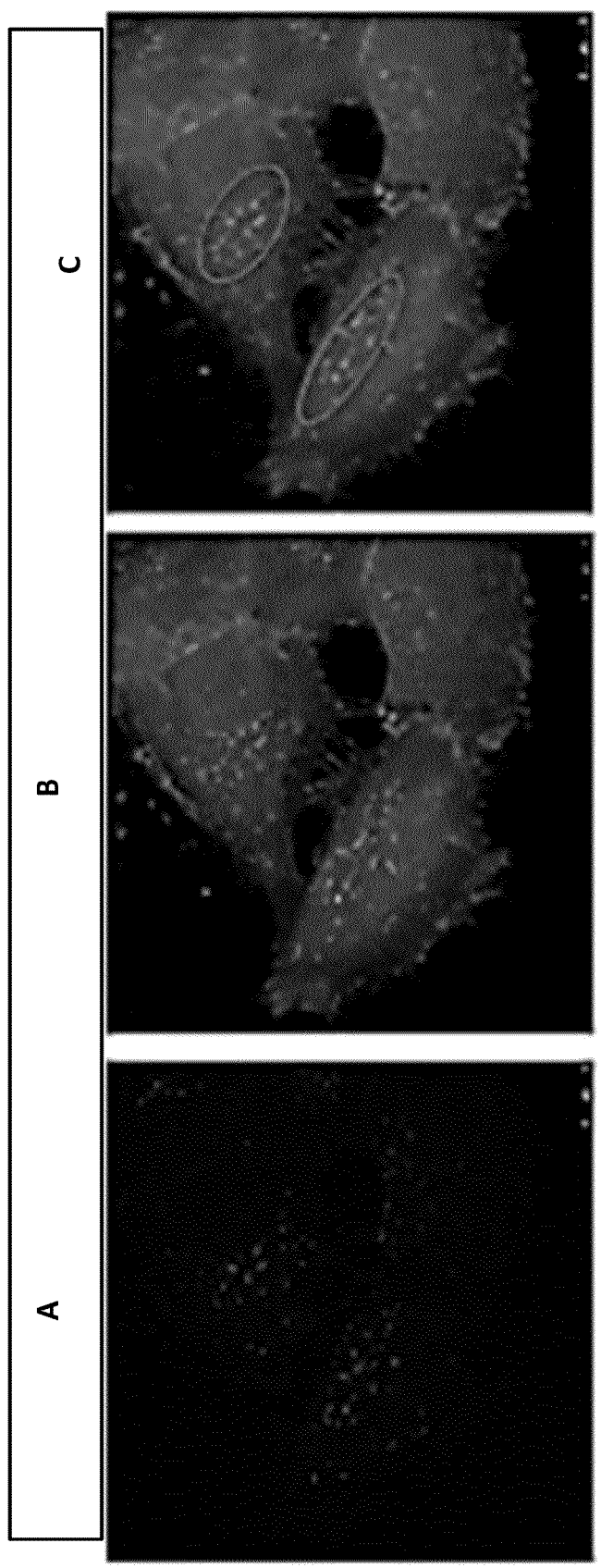
FIGS. 4A-4B are confocal microscopy images of HeLa cells at 63× magnification in accordance with one or more embodiments of the present disclosure. A) Image of lipid rafts, $\lambda_{ex/em}$=594/625 nm; B) image of the probe described above for FIG. 3, $\lambda_{ex/em}$=496/525 nm; and C) overlay of A and B with points of greatest co-localization highlighted in circles.

Dual fluorescence microscopy was used to show that the cholesterol moiety efficiently anchors the SEQ ID NO: 1 peptide to HeLa cell membranes and concentrates it in lipid raft domains (see FIG. 4). This is consistent with previous reports in which cholesterol was used in this role.[17,22] Fluorescein-labeled SEQ ID NO: 1 peptide without the cholesterol anchor was not visible using fluorescence microscopy, indicating that the peptide alone does not localize in cells. Lipid rafts were labeled with fluorescently tagged cholera toxin subunit B that selectively binds to a raft-specific protein, $G_{M1}$. FIGS. 4A and 4B show confocal microscopy images of HeLa cells at 63× magnification. A) Image of lipid rafts, $\lambda_{ex/em}$=594/625 nm; B) image of the probe described above for FIG. 3, $\lambda_{ex/em}$=496/525 nm; and C) overlay of A and B with points of greatest co-localization highlighted in circles.

Example 2

Use of β-MAP to Monitor In Vitro BACE Activity

Figure 5:
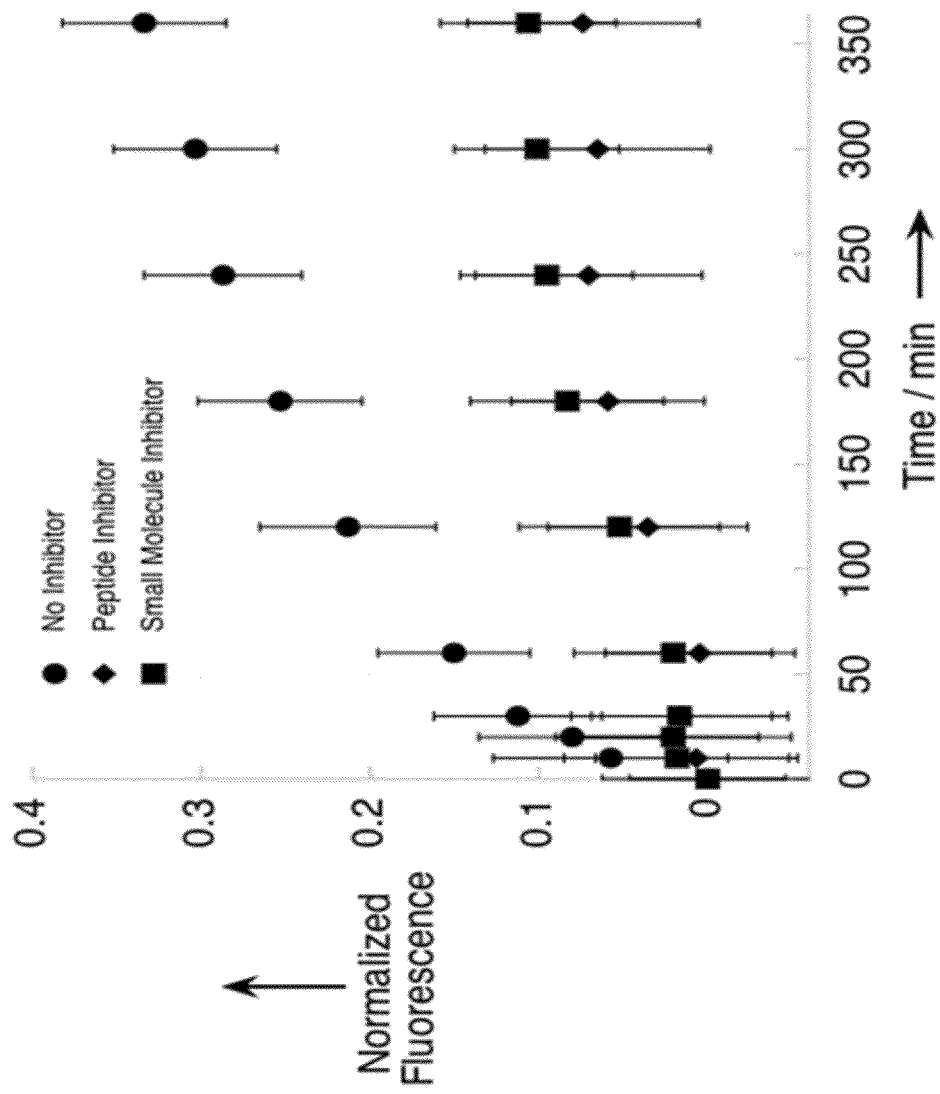
FIG. 5 is a graph showing BACE molecular probe β-MAP used to evaluate two commercial BACE inhibitors in vitro, a peptide small molecule inhibitor Peptide β-Secretase Inhibitor III and small molecule BACE inhibitor AXON 1125 in accordance with one or more embodiments of the present disclosure. A suppressed fluorescence signal denotes effective enzyme inhibition. Each condition was evaluated in triplicate. Experiments were performed at 37° C. in 0.1M sodium acetate buffer pH4.5 with 10 μM β-MAP and 10 μM inhibitor.

The BACE molecular probe β-MAP can be used to monitor in vitro BACE hydrolysis similar to many other FRET probes reported in the literature.[23] As shown in FIG. 5, an in vitro evaluation of two commercially available BACE inhibitors (one small molecule, and one peptide) yielded expected results. Specifically, 5 mM stock solutions of the FRET probe β-MAP, Peptide β-Secretase Inhibitor III (EMD), and small molecule BACE inhibitor AXON 1125 (AXON MEDCHEM) were prepared by dissolving lyophilized powder in DMSO. Stock solutions were diluted to 10 µM in 200 µL 0.1M Sodium Acetate Buffer pH4.5 (0.2-0.4% DMSO) in triplicate in 96-well plates. Solution was aspirated by pipette 3× to ensure proper mixing. 4 µL purified BACE ectodomain was added to each well and fluorescence was recorded on a plate reader at 37° C. every 10 min using 355 nm and 460 nm excitation/emission filters respectively. Fluorescence data was normalized to a blank buffer solution. A suppressed fluorescence signal denotes effective inhibition. Analysis performed in 0.1M sodium acetate buffer pH4.5 with 10 µM β-MAP and 10 µM inhibitors. In the absence of inhibitor, a strong fluorescence turn-on was observed when β-MAP was incubated with BACE corresponding to liberation of the chromophore from the quenching DABCYL group. The cleavage site was confirmed through identification of the products via LC-MS. When an inhibitor was added to the reaction mixture, the turn-on signal was significantly attenuated in both cases (see FIG. 5).

Example 3

Use of β-MAP BACE Probe to Monitor In Vivo BACE Activity

The following experiments were performed to demonstrate that the BACE molecular probes such as β-MAP can be used to monitor BACE activity in live cells.

Figure 6:
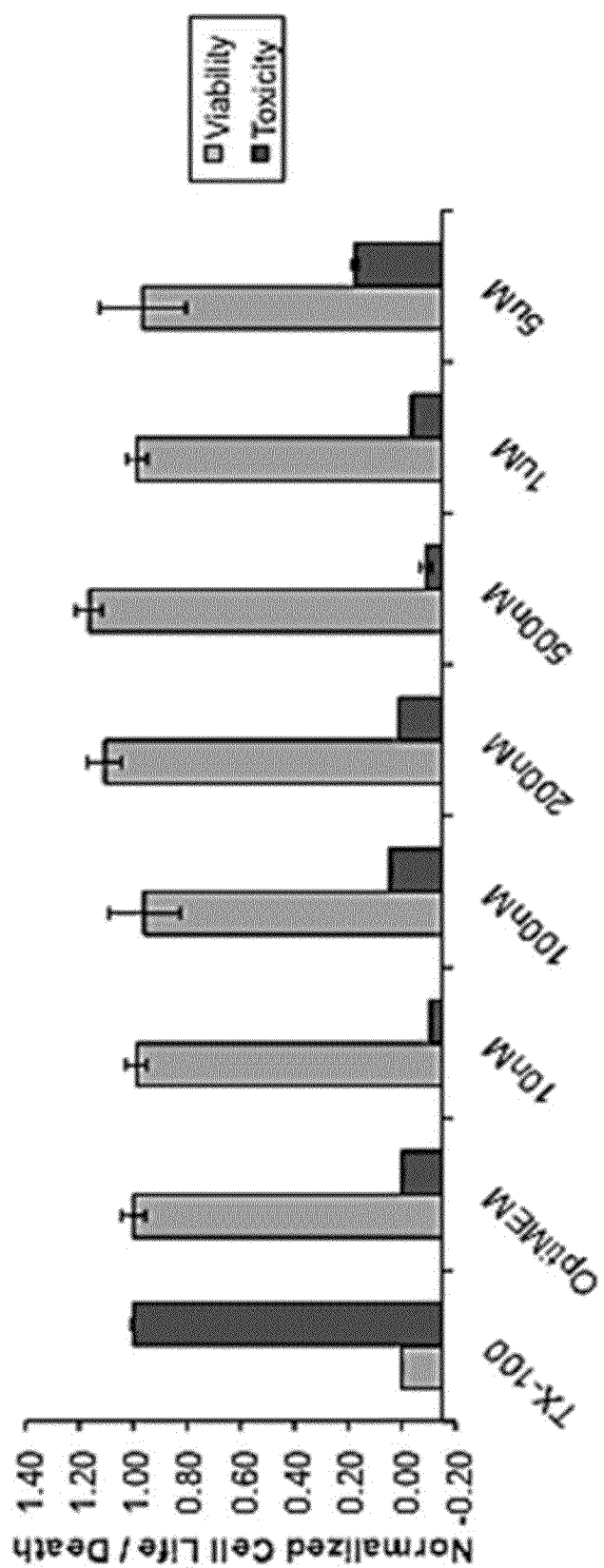
FIG. 6 is a graph showing cell viability in the presence of β-MAP at concentrations ranging from 0-5 μM in accordance with one or more embodiments of the present disclosure. Cells were dosed with β-MAP in 0.1% DMSO for 10 min in acidified OptiMEM after which media was removed and replaced with pH7.4 OptiMEM for 24 hr. TX-100 represents cells treated with 1% Triton X-100 (negative control) and OptiMEM contains no β-MAP (positive control). Cell Viability (light gray) and Cell Toxicity (dark gray) confirm β-MAP is non-toxic over the range of concentrations tested.

First, experiments were performed to show that the β-MAP probe could be used in a manner that would not be toxic to cells. HeLa cells were plated in 2 mL complete growth media in a 24-well plate and allowed to grow to 70% confluence. On the day of the experiment, 1M HCl was added dropwise to an OptiMEM stock solution to pH4.5. Varied concentrations of β-MAP were diluted in DMSO, then diluted further into pH4.5 OptiMEM so the final concentration of DMSO in each condition was 0.1%. Media was removed and cells were washed 1× with PBS. 1 mL of β-MAP in acidified OptiMEM was added to the cells and allowed to incubate at 37° C. and 5% $CO_2$ for 10 min. Treatments were removed and 1 mL of unmodified pH7.4 OptiMEM was added to the cells. Each condition was repeated in triplicate. After 24 h incubation, determination of cell viability was performed using CELLTITER-BLUE (PROMEGA) and cell death using LDH Cytotoxicity Detection Kit (ROCHE). Both protocols were performed according to manufacturer's instructions. β-MAP was shown to be non-toxic over the range of concentrations tested (see FIG. 6). Cell Viability (light gray) and Cell Toxicity (dark gray) confirm β-MAP is non-toxic over the range of concentrations tested.

Figure 7:
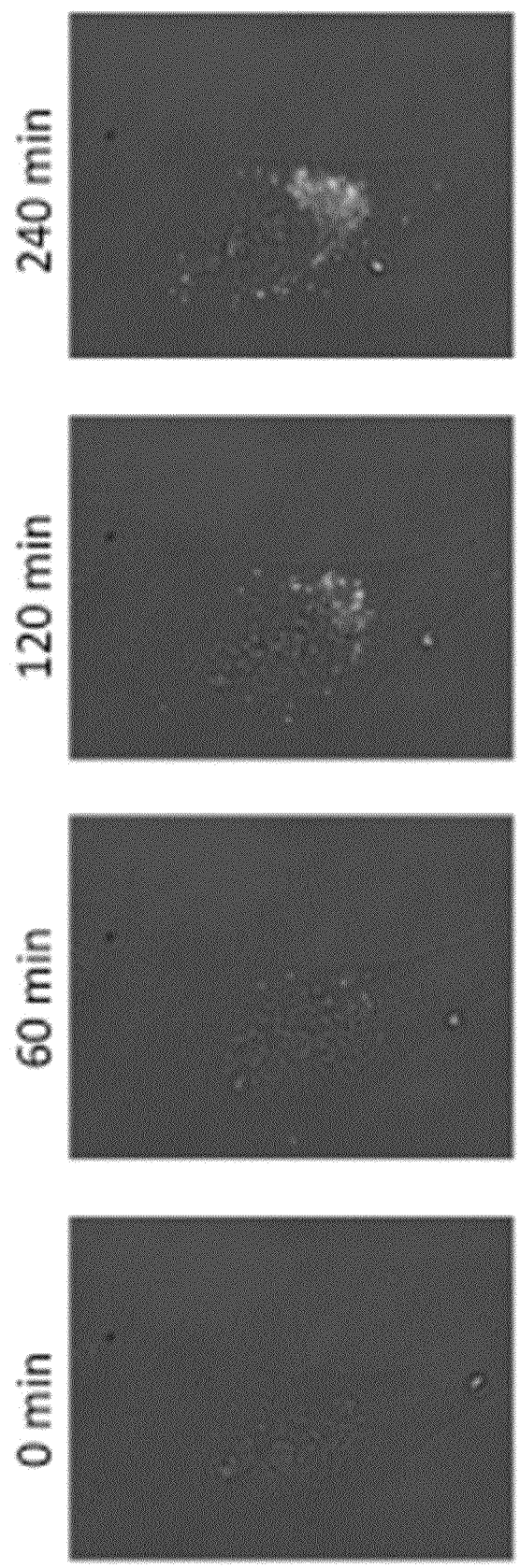
FIG. 7 shows a series of time-lapse images of live HeLa cells treated for 10 min with 200 nM β-MAP before media was replaced with OptiMEM according to one or more embodiments of the present disclosure. Images are 60× Fluorescence images ($\lambda_{ex/em}$=390/470 nm) overlaid with brightfield view shown for 0, 60, 120, and 240 min.

Next a time lapse experiment was performed to show the effect of incubating β-MAP with live HeLa cells. HeLa cells were seeded onto an 8 well µ-slide (IBIDI) in 300 µL complete growth media and allowed to grow to 50% confluence. Media was removed and cells were washed 1× with PBS. 200 nM β-MAP was added in pH4.5 OptiMEM and allowed to incubate for 10 min at 37° C. and 5% $CO_2$. Treatments were removed and replaced with pH7.4 OptiMEM. Cells were visualized on a DELTAVISION ELITE microscope with 60× (oil) or 20× (dry) objectives. Microscope incubation chamber was held at 37° C. and cells were blanketed with a 5% $CO_2$: 95% air mixture. Excitation (390 nm) and emission (470 nm) filters were used to collect images every 10 min for 5-6 hrs. Continuous exposure to the excitation wavelength induced cell death at later time-points. FIG. 7 shows a series of 60× fluorescence images overlaid with bright-field view at 0 min, 60 min, 120 min, and 240 min for the HeLa cells treated for 10 min with the β-MAP demonstrating the fluorescence turn-on effect. When 13-MAP is incubated with live HeLa cells and observed via time-lapse fluorescence microscopy, a strong signal increase is observed in distinct parts of the cell. The DMACA fluorescence signal is easily distinguishable from background noise and fluoresces strongly in acidic intracellular vesicles as well as the more neutral cytoplasm and extracellular space. The signal does not permeate the nucleus of the cell nor does it occur homogeneously across the cell membrane or in the cytoplasm. These observations indicate that hydrolysis is occurring in distinct compartments, which is consistent with the previously reported localization and mechanism of BACE.[24]

Quantitative analysis can be applied to the fluorescence images generated using the BACE probe by integrating the fluorescence density corresponding to β-MAP and plotting versus time. Raw images are pixilated using an appropriate minimum gray value threshold so as not to include cell autofluorescence or background noise. The threshold is kept constant for all images within each stack (set of images at one location over different time points), but vary slightly between stacks because of different focusing parameters. The threshold for each stack is determined at later time points (>4 h) where the signal is brightest to ensure background fluorescence is not included in the integration. Analyzing the pixilated images using Fiji image software yields the area of all pixels above the preset threshold and their average gray value. Multiplying the total area by the average gray value gives the total integrated density of the fluorescence image. The number of cells in each image is important as quantification of the overall fluorescence signal is dependent on the number of cells in view. Care was taken to ensure that each stack selected for processing contained about the same number of cells. Additionally 20x magnification was used to encompass more cells per image and obtain more statistically relevant results. Finally, by plotting the total integrated density of each image versus its corresponding time point, a graphical representation of the fluorescence turn-on is attained.

In order to verify that the fluorescence turn-on effect observed for the FIG. 7 experiment was BACE mediated and not the result of non-specific cleavage, siRNA was used to knockdown BACE expression in HeLa cells. The experiment was performed by plating cells in 2, 6-well plates and allowing the cells to grow to 50% confluence in complete growth media. 1 day before transfection, the media was replaced with DMEM containing 10% fetal bovine serum without antibiotics. Three BACE specific siRNA sequences (STEALTH siRNA, INVITROGEN) were transfected using DHARMAFECT I (THERMO) in OptiMEM (GIBCO) for 1 day according to manufacturer's instructions. After transfection, media was replaced with complete growth media. One 6-well plate was designated for western blot as described below while the cells in the second plate were trypsinized, pelleted by centrifugation, and transferred to an 8-well μ-slide (IBIDI) for microscopy.

BACE expression for each condition was analyzed by Western Blot according to the following procedure. The cells were washed with ice-cold PBS, harvested in PBS, and centrifuged for 1 min. Whole-cells lysate was isolated using RIPA buffer (50 mM Tris, pH8.0, 200 mM NaCl, 1.5 mM $MgCl_2$, 1% NP-40, 1 mM EGTA, 10% Glycerol, 50 mM NaF, 2 mM $Na_3VO_4$, protease inhibitor cocktail 1:200), and protein concentration of whole-cell lysate was determined using BIO-RAD BRADFORD reagent using bovine serum albumin (BSA) for standard curve production. For each sample, proteins were resolved by SDS-PAGE and transferred to a PVDF membrane (BIORAD). The membrane was blocked with 5% milk in Tris-Buffered Saline and Tween 20 (TBST) buffer for 2 hrs at room temperature and then incubated with primary antibody (1:1000 (84 antibody: 8 mL 5% milk) for BACE (SIGMA, Anti-BACE N-termius), and 1:4000 for β-actin (SIGMA, MONOCLONAL ANTI-BETA ACTIN) overnight at 4° C. The membrane was washed with TBST buffer for 10 min three times, incubated with HRP conjugated secondary antibody (1:5000 in 5% milk) for 1 hr at room temperature, and washed with TBST. The blot was then developed using ECL reagent.

Figure 8:
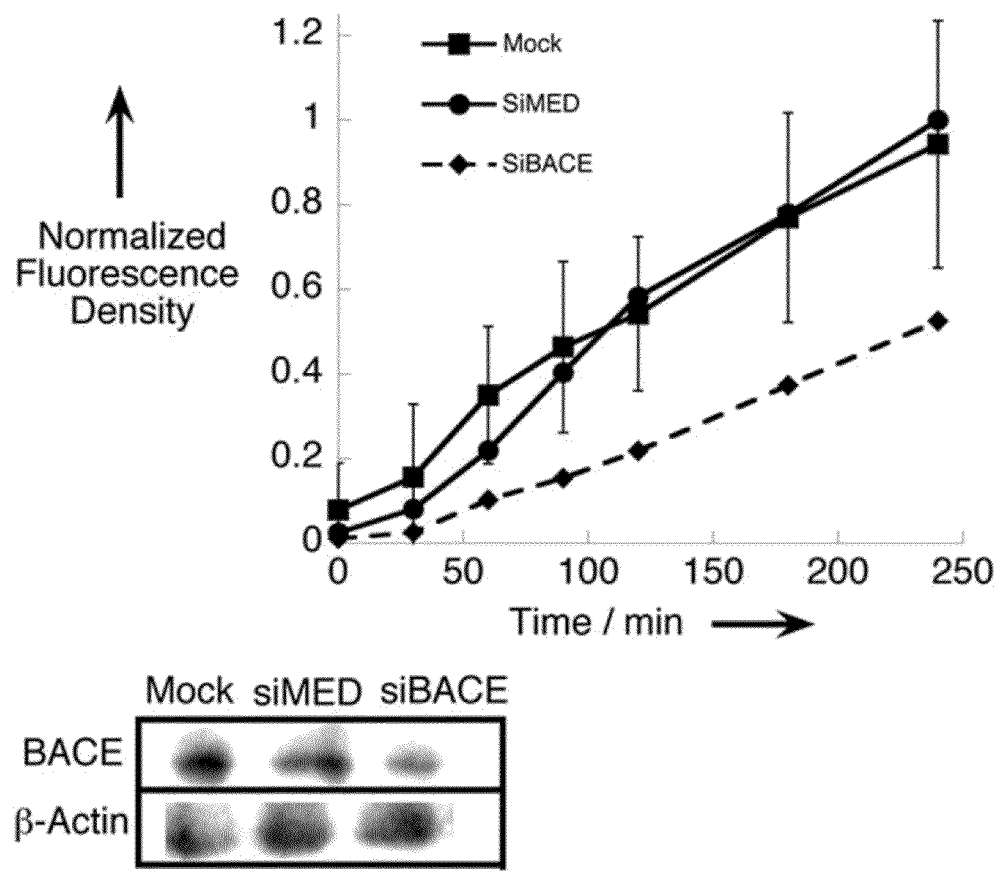
FIG. 8 is a graph showing that HeLa cells transfected with BACE-specific siRNA exhibit a diminished capacity to cleave β-MAP compared to untreated controls in accordance with one or more embodiments of the present disclosure. HeLa cells transfected with BACE-specific siRNA exhibit a diminished capacity to cleave β-MAP, as demonstrated by the fluorescence progress curves (top). The level of BACE expression for each condition was analyzed by Western blot with 6-Actin used as a loading control (bottom). Mock: Untreated control, siMED: scrambled control siRNA, siBACE: BACE-specific siRNA.

As seen in FIG. 8, HeLa cells transfected with BACE-specific siRNA exhibited a diminished capacity to cleave β-MAP compared to untreated controls or a control treated with a scrambled siRNA sequence (siMED). BACE expression for each condition was analyzed by Western Blot with the representative BACE band shown in relation to β-Actin as a loading control.

Figure 9:
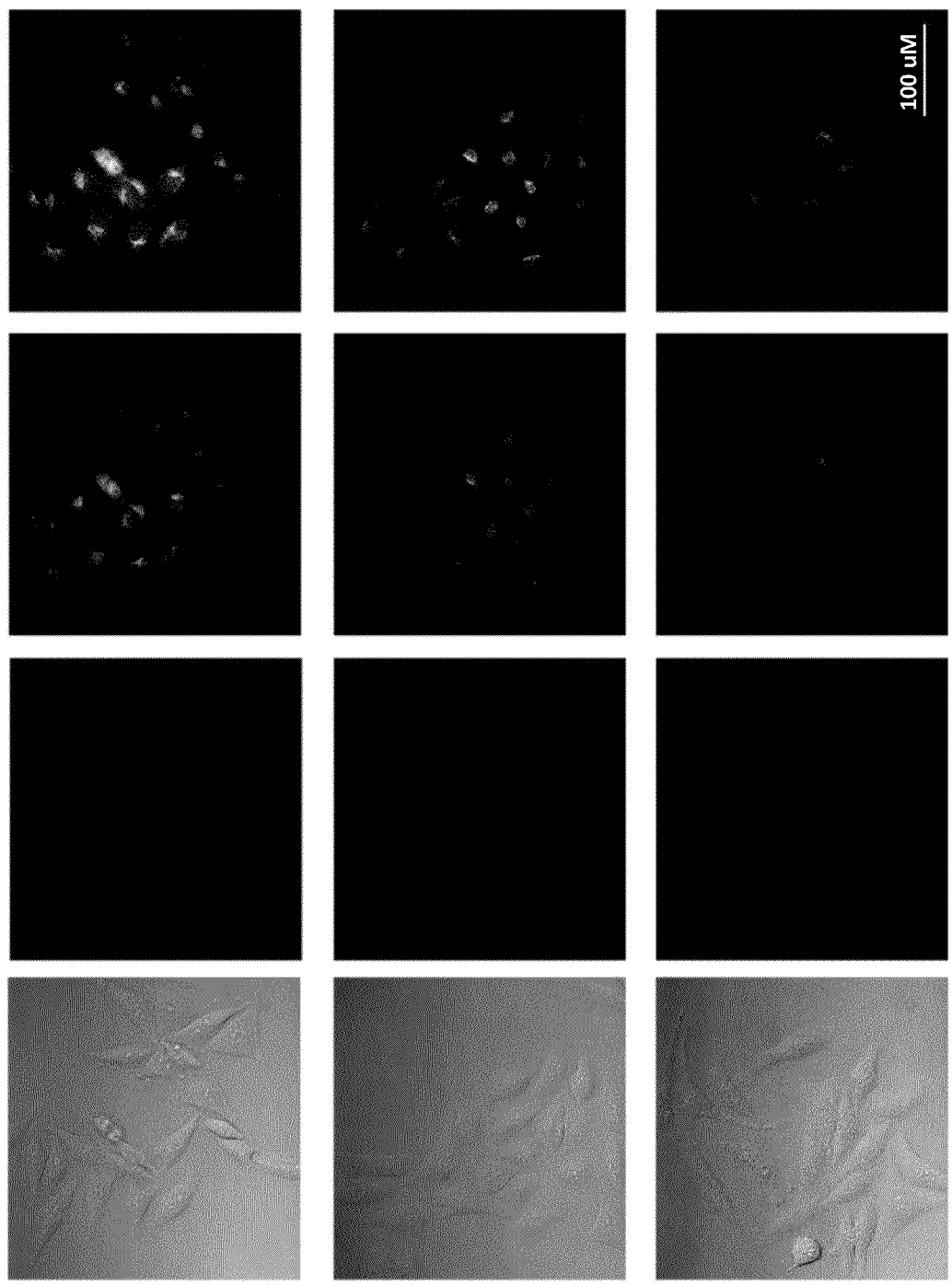
FIG. 9 is a series of panels showing time-lapse fluorescence images of HeLa cells treated with 200 nM β-MAP and 5 nM (middle row) or 2.5 μM (bottom row) of a small molecule BACE inhibitor AXON 1125 (AXON MEDCHEM) for 10 min and then the images show sequential time points after removal of the β MAP and BACE inhibitor from the cells in accordance with one or more embodiments of the present disclosure. The 4 columns of panels shown are images of the cells from left to right of Bright Field, 0 minutes, 100 minutes, and 160 minutes, respectively.

To further explore the scope of the use of BACE probes in live cells, HeLa cells were treated with β-MAP and both the peptide and small molecule inhibitors as described above and imaged at 20x magnification. The experiment was performed by seeding HeLa cells onto an 8 well μ-slide (IBIDI) in 3004 complete growth media and allowing the cells to grow to 50% confluence. Media was removed and cells were washed 1x with PBS. 200 nM β-MAP was added in pH4.5 OptiMEM (0.1% DMSO) with BACE inhibitors and allowed to incubate for 10 min at 37° C. and 5% $CO_2$. Treatments were removed and replaced with pH7.4 OptiMEM containing inhibitors. Cells were visualized on a DELTAVISION ELITE microscope with 60x (oil) or 20x (dry) objectives. Microscope incubation chamber was held at 37° C. and cells were blanketed with a 5% $CO_2$: 95% air mixture. Excitation (390 nm) and emission (470 nm) filters were used to collect images every 10 min for 5-6 hrs. Continuous exposure to the excitation wavelength induced cell death at later time-points. FIG. 9 shows the time-lapse fluorescence images of the HeLa cells treated with 200 nM (3-MAP and varied concentrations of the small molecule BACE inhibitor AXON 1125 5 nM (middle row) or 2.5 μM (bottom row for 10 min and then the images show sequential time points after removal of the (3-MAP and BACE inhibitor from the cells. The 4 columns of panels shown are images of the cells from left to right of Bright Field, 0 minutes, 100 minutes, and 160 minutes, respectively. Qualitative analysis of the fluorescence images shows that when cells are treated with the small molecule inhibitor, a dose dependent decrease in the fluorescence signal is observed (FIGS. 9, $2^{nd}$ and $3^{rd}$ rows). Conversely, when cells are treated with the peptide BACE inhibitor, the fluorescence intensity is relatively constant across all doses tested, indicating it is not an effective inhibitor of BACE activity in cells (data not shown). Though both inhibitors are effective in vitro, only the small molecule inhibitor has cellular efficacy,[15a] as the peptide is unable to access the endosomal compartments where BACE is active.

Figure 10:
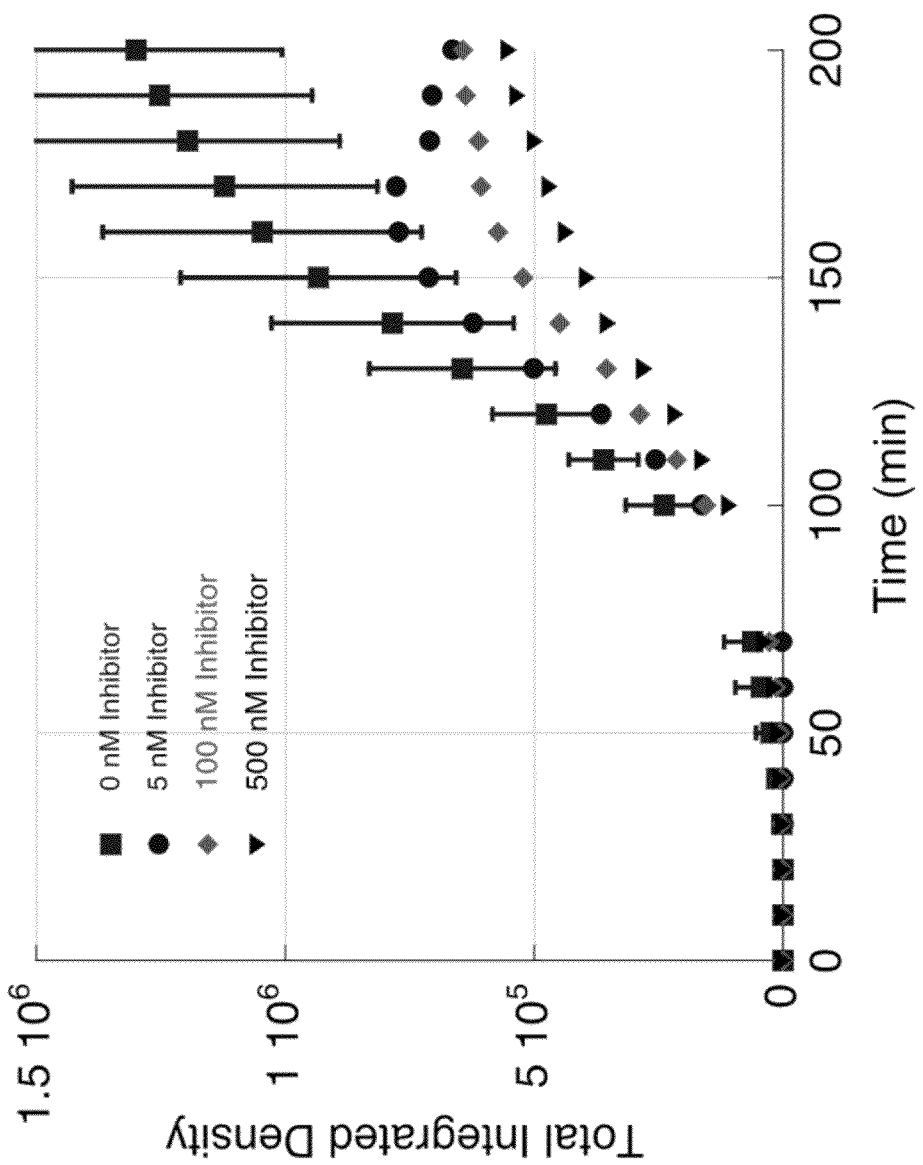
FIG. 10 is a graph showing that incubation of BACE probe β-MAP live HeLa cells in the presence of various concentrations of small molecule BACE inhibitor AXON 1125 results in a dose dependent decrease in the fluorescence signal in accordance with one or more embodiments of the present disclosure. Progress curves represent the average of three independent trials.

Using the previously described quantitative analysis approach, the effectiveness of each inhibitor was evaluated across a range of concentrations. Cells treated with small molecule BACE inhibitor AXON 1125 in the presence of BACE probe β-MAP demonstrated a decreased fluorescence signal compared to untreated controls. FIG. 10 shows the progress curves for selected concentrations of the small molecule BACE inhibitor. By calculating the slope of each curve from 100-150 minutes a rate of hydrolysis was determined at each inhibitor concentration. As described herein previously, similar analysis of images taken for experiments using the peptide BACE inhibitor (tested at 100 nM, 500 nM, and 0.5 μM concentrations) yielded no significant differences in the fluorescence, confirming its lack of effectiveness in cells (data not shown).

Even at high concentrations of inhibitor the fluorescence response from the BACE probe is not completely abolished. This observation suggests the probe is not strictly specific for BACE and that some nonspecific cleavage is most likely occurring. This supposition is also supported by observations that the fluorescence response from cells treated with higher concentrations of probe (5 μM) is not nearly as attenuated in the presence of inhibitors (data not shown). Cathepsin-D and renin are two aspartyl proteases that are structurally related to BACE and could be responsible for this nonspecific hydrolysis. The membrane anchored peptide inhibitor from which β-MAP was modeled also showed non-specific efficacy at concentrations above 200 nM.[17]

The BACE probes described herein represent a novel method for evaluating BACE activity in living cells. The design of the probes allow for anchoring to lipid raft domains within the cell membrane, endocytosis into vesicles, and cleavage by BACE in the same way as the BACE natural substrate APP. Hydrolysis of the BACE probes of the present disclosure can produce a fluorescence turn-on signal that can be easily monitored via fluorescence microscopy. This strategy permits identification of not only where BACE hydrolysis is occurring, but to what extent.

The β-MAP BACE probe was used to confirm the effectiveness of a previously reported BACE inhibitor. Because of the ease of use and applicability to unaltered cells of the BACE probes of the present disclosure, the BACE probes can also be used to efficiently screen libraries of other potential BACE inhibitors. The probes can also be used to evaluate how external stimuli may affect BACE activity without changing expression levels. It has been suggested that heparin analogues influence BACE activity by binding to and displacing an occluding loop near the BACE active site, thus allowing increased substrate interactions.[25] While this would imply heparin treatment may increase the amount of Aβ produced and enhance toxicity, an opposite effect is observed experimentally.[26] Clearly further research is required in this, as well as many other areas related to AD. BACE probes such as, for example, β-MAP that can expedite research and deepen our understanding of the molecular players involved, play a crucial role in the development of therapeutics to combat this debilitating disease.

Example 4

Synthesis Procedures

Materials and Instrumentation

All chemicals and solvents were obtained from SIGMA-ALDRICH and used without further purification unless otherwise noted. All water was nanopure. Peptides were synthesized on a PROTEIN TECHNOLOGIES PS3 automated peptide synthesizer. Liquid chromatography-electrospray mass spectrometry (LC-MS) data were collected on an AGILENT 1100 Series HPLC in line with a LC/MSD trap and a DALY conversion dynode detector. In vitro BACE assays were conducted on a PERKIN ELMER VICTOR 1420 plate reader. Fluorescence data were recorded on a FLUOROLOG-3 fluorimeter from HORIBA Jobin Yvon. Dynamic light scattering data were collected on a DYNAPRO TITAN from WYATT TECHNOLOGY CORPORATION. Fluorescence microscopy was performed on a DELTAVISION ELITE deconvolution microscope with temperature, humidity, and $CO_2$ control. Lipid raft colocalization studies were performed on a LEICA SP5 confocal microscope with a live cell chamber. All fluorescence images were processed using FIJI image software.

Peptide Synthesis

The precursor compound Fmoc-Asp(dihydrocholesterol)-OH was synthesized by esterification of the side chain of Fmoc-Asp-OtBu (NOVABIOCHEM) with 5α-Cholestan-3β-ol using MSNT/N-Methylimidazole in dichloromethane. Coupling was performed with dry solvents under argon. Deprotection with TFA yielded the Fmoc-Asp(Chol)-COOH building block. Fmoc-NH-(Peg)$_4$-COOH (NOVABIOCHEM) was dissolved in DMF with sonication before use. Fmoc-Lys(DABCYL)-OH (ANASPEC) and DMACA (ANASPEC) were used without modification. For lipid raft studies, 5(6) carboxyfluorescein was coupled to the N-terminus of the peptide under standard conditions.

Peptides were synthesized in 0.1 mmol scale on PAL-PEG-PS resin (APPLIED BIOSYSTEMS). Standard Fmoc (9-fluorenylmethoxy-carbonyl)-protected natural and non-natural amino acids (CHEM-IMPEX and NOVABIOCHEM) were coupled in 20 min cycles with HBTU (O-benzotriazole-N,N,N',N'-tetramethyluronium hexafluorophosphate) (NOVABIOCHEM) and N-methylmorpholine (NMM) (ACROS) in N,N'-dimethylformamide (DMF) (CALEDON). Fmoc protecting groups were removed by using 20% piperidine in DMF. Cleavage from the resin and removal of side chain protecting groups was accomplished by treating resin with a 10-mL mixture of 95% trifluoroacetic acid (TFA) and 2.5% triisopropylsilane (TIS) under nitrogen while shaking for 4 hr. Peptide was precipitated from solution by evaporating off TFA with a nitrogen stream, followed by three washes with diethyl ether (CALEDON). Purification was accomplished by semi-preparative reversed-phase HPLC on a WATERS SPHERISORB S10 C8 column with a linear 40 min gradient from 7 to 70% acetonitrile in water with 0.1% TFA. Purity was validated to be greater than 90% by analytical HPLC. Mass of each peptide was determined by ESI-MS. Peptides were stored as lyophilized powder at −20° C. until use.

Figure 11:
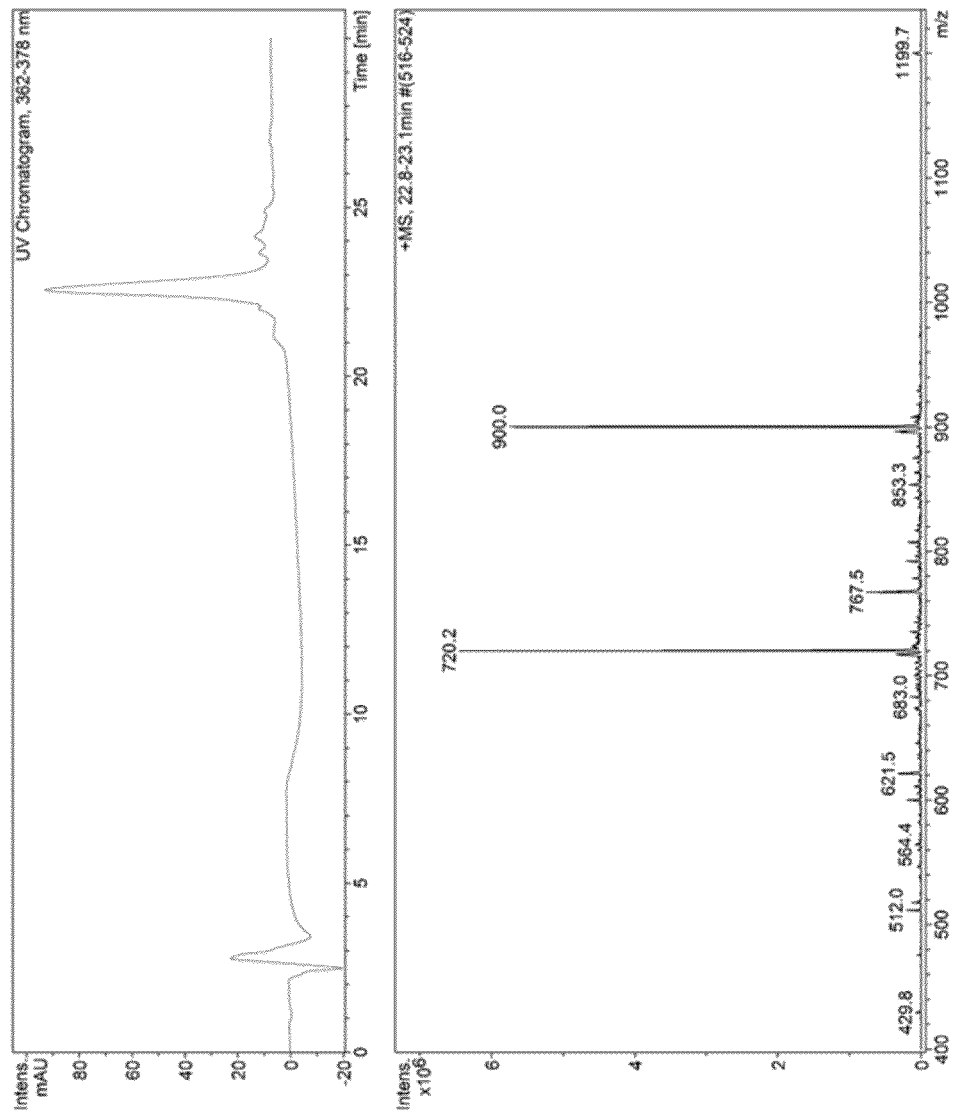
FIG. 11 is an analytical UV and a mass spectrometry chromatogram after purification of β-MAP (shown in FIG. 1) in accordance with one or more embodiments of the present disclosure. HPLC run on ECLIPSE XDB-C8 column with 0.1% formic acid $H_2O$: Acetonitrile gradient. ESI-MS data show peaks that correspond to the +3H, +4H, and +5H ions of a parent compound with a mass of 3596.0, which matches the expected average mass of 3596.2 for β-MAP. The expected average molecular weight was 3596 and the observed molecular mass (m) was 3596.0.

FIG. 11 shows an analytical UV and a mass spectrometry chromatogram after purification of β-MAP (shown in FIG. 1). HPLC run on ECLIPSE XDB-C8 column with 0.1% formic acid H$_2$O: Acetonitrile gradient. ESI-MS data show peaks that correspond to the +3H, +4H, and +5H ions of a parent compound with a mass of 3596.0, which matches the expected average mass of 3596.2 for β-MAP. The expected average molecular weight was 3596 and the observed molecular mass (m) was 3596.0.

Figure 12:
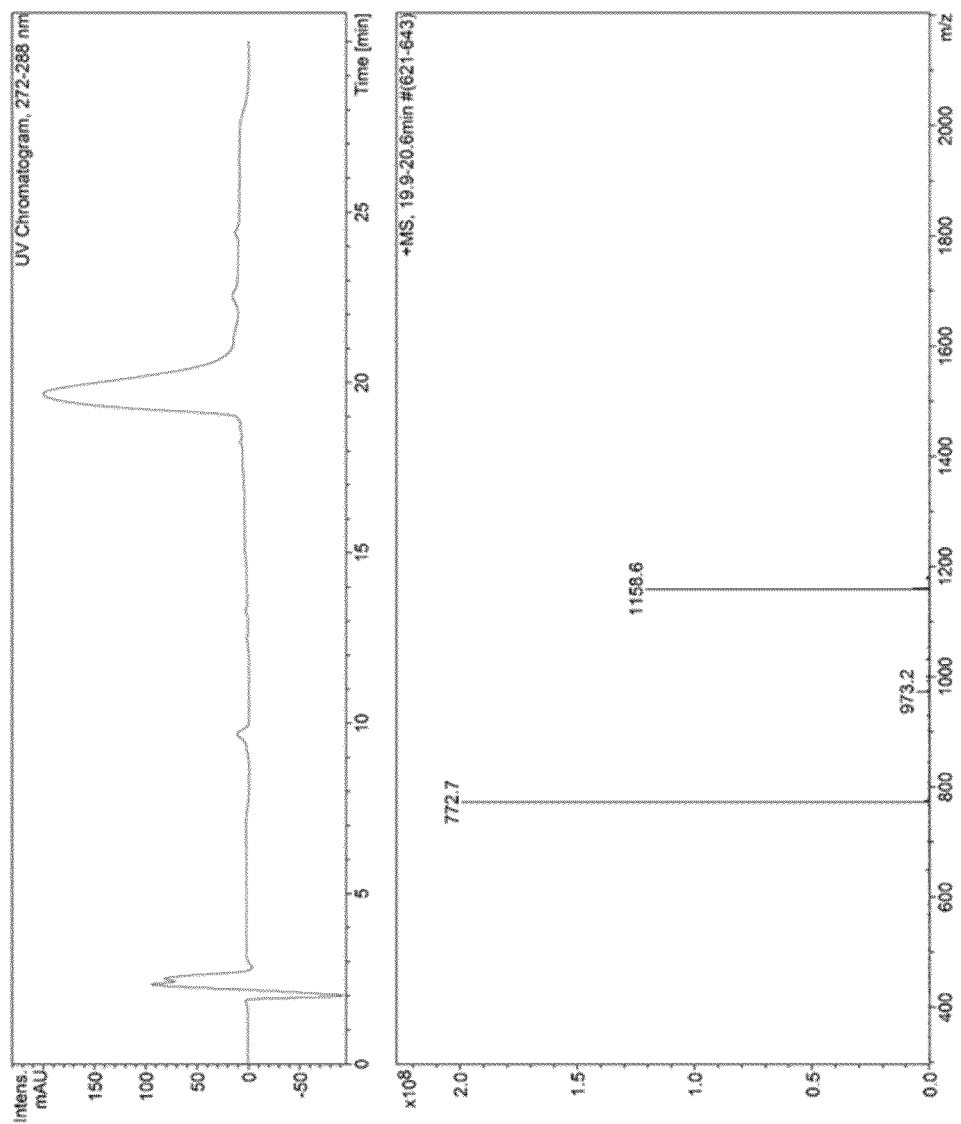
FIG. 12 is analytical UV and a mass spectrometry chromatogram after purification of cholesterol anchored SEQ ID NO: 1 peptide with fluorescein tagged to the N-terminus (shown in FIG. 3) in accordance with one or more embodiments of the present disclosure. HPLC run on ECLIPSE XDB-C8 column with 0.1% formic acid $H_2O$: Acetonitrile gradient. ESI-MS data show peaks that correspond to the +2H and +3H ions of a parent compound with a mass of 2315.2. This agrees with the expected average mass of 2315.6 for this peptide. The expected average molecular weight was 2315.6 and the observed molecular mass (m) was 2315.2.

FIG. 12 shows an analytical UV and a mass spectrometry chromatogram after purification of cholesterol anchored SEQ ID NO: 1 peptide with fluorescein tagged to the N-terminus (shown in FIG. 3). HPLC run on ECLIPSE XDB-C8 column with 0.1% formic acid H$_2$O: Acetonitrile gradient. ESI-MS data show peaks that correspond to the +2H and +3H ions of a parent compound with a mass of 2315.2. This agrees with the expected average mass of 2315.6 for this peptide. The expected average molecular weight was 2315.6 and the observed molecular mass (m) was 2315.2.

Figure 13:
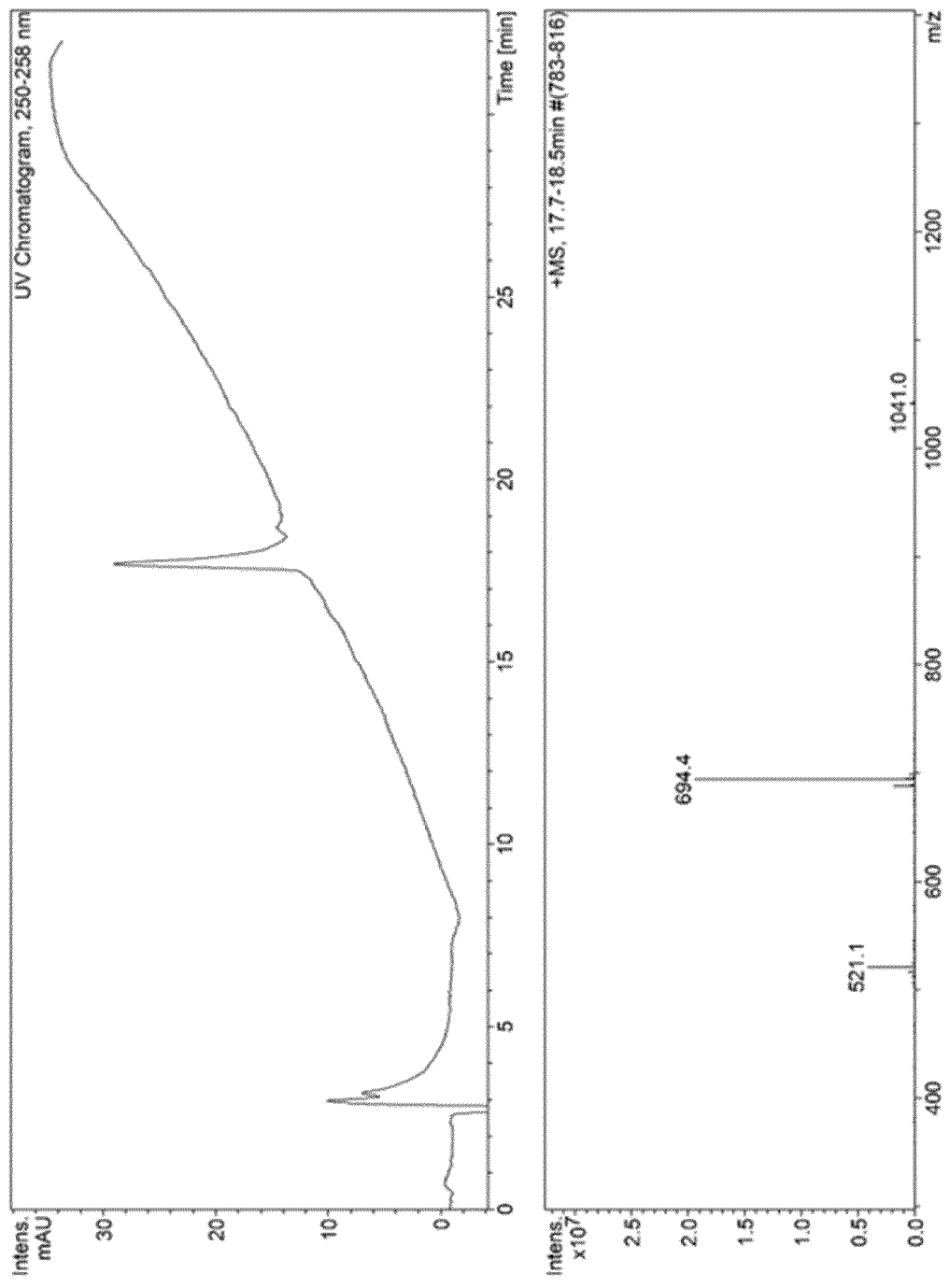
FIG. 13 is an analytical UV and a mass spectrometry chromatogram after purification of DMACA-SEQ ID NO: 1-K-

FIG. 13 shows an analytical UV and a mass spectrometry chromatogram after purification of DMACA-SEQ ID NO: 1-K-DABCYL HPLC run on Eclipse XDB-C8 column with 0.1% formic acid H$_2$O: Acetonitrile gradient. ESI-MS data show peaks that correspond to the +2H, +3H, and +4H ions of a parent compound with a mass of 2080.2. This agrees with the expected average mass of 2080.3 for this peptide. The expected average molecular weight was 2080.3 and the observed molecular mass (m) was 2080.2

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

[1] J. Hardy, D. Selkoe, *Science* 2002, 297, 353-356.
[2] aA. Rauk, *Dalton Transactions* 2008, 1273-1282; bP. Crouch, S. Harding, A. White, J. Camakaris, A. Bush, C. Masters, *International Journal of Biochemistry & Cell Biology* 2008, 40, 181-198.
[3] M. Bolognesi, R. Matera, A. Minarini, M. Rosini, C. Melchiorre, *Current Opinion in Chemical Biology* 2009, 13, 303-308.
[4] G. Evin, A. Barakat, C. Masters, *International Journal of Biochemistry & Cell Biology* 2010, 42, 1923-1926.
[5] V. Frisardi, V. Solfrizzi, V. Imbimbo, C. Capurso, A. D'Introno, A. Colacicco, G. Vendemiale, D. Seripa, A. Pilotto, A. Capurso, F. Panza, *Current Alzheimer Research* 2010, 7, 40-55.
[6] M. SHOJI, T. GOLDE, J. GHISO, T. CHEUNG, S. ESTUS, L. SHAFFER, X. CAI, D. MCKAY, R. TINTNER, B. FRANGIONE, S. YOUNKIN, *Science* 1992, 258, 126-129.
[7] R. Postina, *Current Alzheimer Research* 2008, 5, 179-186.
[8] K. Endres, F. Fahrenholz, *Febs Journal* 2010, 277, 1585-1596.
[9] M. Hutton, J. Perez-Tur, J. Hardy, *Essays in Biochemistry, Vol 33, 1998* 1998, 33, 117-131.
[10] M. Hemming, J. Elias, S. Gygi, D. Selkoe, *Plos One* 2009, 4.
[11] F. Mancini, A. De Simone, V. Andrisano, *Analytical and Bioanalytical Chemistry* 2011, 400, 1979-1996.
[12] aM. Congreve, D. Aharony, J. Albert, O. Callaghan, J. Campbell, R. Carr, G. Chessari, S. Cowan, P. Edwards, M. Frederickson, R. McMenamin, C. Murray, S. Patel, N. Wallis, *Journal of Medicinal Chemistry* 2007, 50, 1124-1132; bY. Cheng, T. Judd, M. Bartberger, J. Brown, K. Chen, R. Fremeau, D. Hickman, S. Hitchcock, B. Jordan, V. Li, P. Lopez, S. Louie, Y. Luo, K. Michelsen, T. Nixey, T. Powers, C. Rattan, E. Sickmier, D. St Jean, R. Wahl, P. Wen, S. Wood, *Journal of Medicinal Chemistry* 2011, 54, 5836-5857; cD. Huang, U. Luthi, P. Kolb, M. Cecchini, A. Barberis, A. Caflisch, *Journal of the American Chemical Society* 2006, 128, 5436-5443; dY. Shimmyo, T. Kihara, A. Akaike, T. Niidome, H. Sugimoto, *Biochimica Et Biophysica Acta-General Subjects* 2008, 1780, 819-825; eW. Yang, W. Lu, Y. Lu, M. Zhong, J. Sun, A. Thomas, J. Wilkinson, R. Fucini, M. Lam, M. Randal, X. Shi, J. Jacobs, R. McDowell, E. Gordon, M. Ballinger, *Journal of Medicinal Chemistry* 2006, 49, 839-842.
[13] aS. B. Halima, L. Rajendran, *Journal of Alzheimer's Disease* 2011, 24, 143-152; bF. Gruninger-Leitch, D. Schlatter, E. Kung, P. Nelbock, H. Dobeli, *Journal of Biological Chemistry* 2002, 277, 4687-4693; cS. Stachel, C. Coburn, D. Rush, K. Jones, H. Zhu, H. Rajapakse, S. Graham, A. Simon, M. Holloway, T. Allison, S. Munshi, A. Espeseth, P. Zuck, D. Colussi, A. Wolfe, B. Pietrak, M. Lai, J. Vacca, *Bioorganic & Medicinal Chemistry Letters* 2009, 19, 2977-2980.
[14] P. May, R. Dean, S. Lowe, F. Martenyi, S. Sheehan, L. Boggs, S. Monk, B. Mathes, D. Mergott, B. Watson, S. Stout, D. Timm, E. LaBell, C. Gonzales, M. Nakano, S. Jhee, M. Yen, L. Ereshefsky, T. Lindstrom, D. Calligaro, P. Cocke, D. Hall, S. Friedrich, M. Citron, J. Audia, *Journal of Neuroscience* 2011, 31, 16507-16516.
[15] aS. Stachel, C. Coburn, T. Steele, K. Jones, E. Loutzenhiser, A. Gregro, H. Rajapakse, M. Lai, M. Crouthamel, M. Xu, K. Tugusheva, J. Lineberger, B. Pietrak, A. Espeseth, X. Shi, E. Chen-Dodson, M. Holloway, S. Munshi, A. Simon, L. Kuo, J. Vacca, *Journal of Medicinal Chemistry* 2004, 47, 6447-6450; bX. P. Shi, K. Tugusheva, J. E. Bruce, A. Lucka, E. Chen-Dodson, B. H. Hu, G. X. Wu, E. Price, R. B. Register, J. Lineberger, R. Miller, M. J. Tang, A. Espeseth, J. Kahana, A. Wolfe, M. C. Crouthamel, S. Sankaranarayanan, A. Simon, L. Chen, M. T. Lai, B. Pietrak, J. DiMuzio, Y. M. Li, M. Xu, Q. Huang, V. Garsky, M. K. Sardana, D. J. Hazuda, *Journal of Alzheimers Disease* 2005, 7, 139-148; cH. Yamakawa, S. Yagishita, E. Futai, S. Ishiura, *Journal of Biological Chemistry* 2010, 285, 1634-1642; dM. Oh, S. Kim, Y. Oh, D. Choi, H. Sin, I. Jung, W. Park, *Analytical Biochemistry* 2003, 323, 7-11; eB. Pietrak, M. Crouthamel, K. Tugusheva, J. Lineberger, M. Xu, J. DiMuzio, T. Steele, A. Espeseth, S. Stachel, C. Coburn, S. Graham, J. Vacca, X. Shi, A. Simon, D. Hazuda, M. Lai, *Analytical Biochemistry* 2005, 342, 144-151.
[16] J. Lu, Z. Zhang, J. Yang, J. Chu, P. Li, S. Zeng, Q. Luo, *Biochemical and Biophysical Research Communications* 2007, 362, 25-30.
[17] L. Rajendran, A. Schneider, G. Schlechtingen, S. Weidlich, J. Ries, T. Braxmeier, P. Schwille, J. Schulz, C. Schroeder, M. Simons, G. Jennings, H. Knolker, K. Simons, *Science* 2008, 320, 520-523.
[18] D. S. Folk, K. J. Franz, *Journal of the American Chemical Society* 2010, 132, 4994-4995.
[19] A. Laude, I. Prior, *Molecular Membrane Biology* 2004, 21, 193-205.
[20] S. Kim, J. Yi, Y. Ko, *Journal of Cellular Biochemistry* 2006, 99, 878-889.
[21] D. Riddell, G. Christie, I. Hussain, C. Dingwall, *Current Biology* 2001, 11, 1288-1293.
[22] J. Lenhart, X. Ling, R. Gandhi, T. Guo, P. Gerk, D. Brunzell, S. Zhang, *Journal of Medicinal Chemistry* 2010, 53, 6198-6209.
[23] aS. Bertini, E. Ghilardi, V. Asso, C. Granchi, F. Minutolo, M. Macchia, *Letters in Drug Design & Discovery* 2010, 7, 507-515; bM. Malamas, J. Erdei, I. Gunawan, K. Barnes, M. Johnson, Y. Hui, J. Turner, Y. Hu, E. Wagner, K. Fan, A. Olland, J. Bard, A. Robichaud, *Journal of Medicinal Chemistry* 2009, 52, 6314-6323.
[24] J. Cordy, N. Hooper, A. Turner, *Molecular Membrane Biology* 2006, 23, 111-122.
[25] D. Klayer, M. Wilce, R. Gasperini, C. Freeman, J. Juliano, C. Parish, L. Foa, M. Aguilar, D. Small, *Journal of Neurochemistry* 2010, 112, 1552-1561.
[26] aH. Cui, A. Hung, D. Klayer, T. Suzuki, C. Freeman, C. Narkowicz, G. Jacobson, D. Small, *Plos One* 2011, 6; bL. Hao, Q. Zhang, T. Yu, Y. Cheng, S. Ji, *Brain Research* 2011, 1368, 1-10.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A molecular probe for beta-secretase (BACE), the probe comprising formula (I):

A-B-C-D-E wherein A is a fluorescent group, B is a BACE substrate comprising a polypeptide set forth in SEQ ID NOs:1, 2 or 6, or a conservatively substituted variant thereof, C is a quenching group, D is at least one linker molecule, and E is a cell membrane anchor.

2. The probe according to claim 1, wherein A and C comprise a Fluorescence Resonance Energy Transfer (FRET) pair.

3. The probe according to claim 2, wherein A is a fluorophore selected from the group consisting of 7-dimethylaminocoumarin-4-acetic acid (DMACA), ALEXA 350, dimethylaminocoumarin, 5/6-carboxyfluorescein, ALEXA 488, ATTO 488, DY-505, 5/6-carboxyfluorescein, ALEXA 488, ALEXA 532, ALEXA 546, ALEXA 555, ATTO 488, ATTO 532, tetramethylrhodamine, CY 3, DY-505, DY-547, ALEXA 635, ALEXA 647, ATTO 600, ATTO 655, DY-632, CY 5, DY-647 or CY 5.5

4. The probe according to claim 3, wherein A comprises DMACA.

5. The probe according to claim 2, wherein C comprises a quenching group selected from the group consisting of 4-(dimethylaminoazo)benzene-4-carboxylic acid (DABCYL), BHQ 1, QSY 35, BHQ 2, QSY 9, ATTO 540Q, BHQ 3, ATTO 612Q and QSY 21.

6. The probe according to claim 5, wherein C comprises DABCYL.

7. The probe according to claim 6, wherein the DABCYL is attached to the BACE substrate module through an ε amino group of a lysine residue.

8. The probe according to claim 1, wherein D comprises one or more of $C_6$-$C_{30}$ alkyl groups, $C_6$-$C_{30}$ substituted alkyl groups, polyols, polyethers, polyethyleneglycol (PEG), polyamines, polyamino acids, polysaccharides, and combinations thereof.

9. The probe according to claim 8, wherein D comprises at least three PEG units.

10. The probe according to claim 1, wherein E comprises a cholesterol moiety or a dihydrocholesterol moiety.

11. The probe according to claim 10, wherein the dihydrocholesterol moiety is an aspartate modified dihydrocholesterol moiety.

12. The probe according to claim 10, wherein the cholesterol or the dihydrocholesterol moiety is attached to the linker molecule through a residue having a positive charge.

13. The probe according to claim 12, wherein the residue having a positive charge comprises arginine.

14. The probe according to claim 1, wherein A comprises DMACA, wherein B comprises a BACE substrate polypeptide set forth in SEQ ID NO: 1, wherein C comprises DABCYL, wherein D comprises at least three PEG units, and wherein E comprises a dihydrocholesterol moiety.

15. A method of using a probe of formula (I) according to claim 1 for imaging beta-secretase (BACE) activity in a live cell comprising:
incubating the probe with the live cell; and
exposing the cell to electromagnetic radiation such that a signal produced by the fluorescent group can be detected upon cleavage of the BACE substrate by the BACE activity in the cell.

16. The method according to claim 15, further comprising creating an image from the detected signal.

17. The method according to claim 15, wherein A comprises DMACA, wherein B comprises a BACE substrate polypeptide set forth in SEQ ID NO: 1, wherein C comprises DABCYL, wherein D comprises at least three PEG units, and wherein E comprises a dihydrocholesterol moiety.

18. The method of claim 15, further comprising adding a potential BACE inhibitor to the incubation of the probe with the live cell, wherein a decrease in the signal in the presence of the potential BACE inhibitor indicates inhibition of the BACE activity in the live cell by the potential inhibitor.

19. A method of using a probe of formula (I) according to claim 1 for imaging beta-secretase (BACE) activity in a living organism comprising:
administering the probe to the living organism; and
exposing the organism to electromagnetic radiation such that a signal produced by the fluorescent group can be detected upon cleavage of the BACE substrate by the BACE activity in the organism.

20. The method according to claim 19, further comprising creating an image from the detected signal.

21. The method according to claim 19, wherein A comprises DMACA, wherein B comprises a BACE substrate polypeptide set forth in SEQ ID NO: 1, wherein C comprises DABCYL, wherein D comprises at least three PEG units, and wherein E comprises a dihydrocholesterol moiety.

22. The method of claim 19, further comprising administering a potential BACE inhibitor along with the administration of the probe to the living organism, wherein a decrease in the signal in the presence of the potential BACE inhibitor indicates inhibition of the BACE activity in the living organism by the potential inhibitor.

* * * * *